(12) United States Patent
Lian

(10) Patent No.: US 9,730,714 B2
(45) Date of Patent: Aug. 15, 2017

(54) CUSTOM RADIOGRAPHICALLY DESIGNED CUTTING GUIDES AND INSTRUMENTS FOR USE IN TOTAL ANKLE REPLACEMENT SURGERY

(71) Applicant: George John Lian, Sacramento, CA (US)

(72) Inventor: George John Lian, Sacramento, CA (US)

(*) Notice: Subject to any disclaimer, the term of this patent is extended or adjusted under 35 U.S.C. 154(b) by 1197 days.

(21) Appl. No.: 13/685,536

(22) Filed: Nov. 26, 2012

(65) Prior Publication Data
US 2013/0085499 A1 Apr. 4, 2013

Related U.S. Application Data

(63) Continuation of application No. 12/798,417, filed on Apr. 2, 2010, now Pat. No. 8,337,503.

(60) Provisional application No. 61/212,533, filed on Apr. 13, 2009, provisional application No. 61/270,203, filed on Jul. 6, 2009.

(51) Int. Cl.
| | | |
|---|---|---|
| A61F 5/00 | (2006.01) | |
| A61B 17/17 | (2006.01) | |
| A61B 17/15 | (2006.01) | |
| A61F 2/42 | (2006.01) | |
| A61B 17/16 | (2006.01) | |
| A61F 2/46 | (2006.01) | |
| A61F 2/30 | (2006.01) | |
| A61B 34/10 | (2016.01) | |

(52) U.S. Cl.
CPC ......... *A61B 17/1775* (2016.11); *A61B 17/15* (2013.01); *A61F 2/4202* (2013.01); *A61B 17/1615* (2013.01); *A61B 17/1682* (2013.01); *A61B 2034/108* (2016.02); *A61F 2/4606* (2013.01); *A61F 2002/30616* (2013.01); *A61F 2002/4205* (2013.01); *A61F 2002/4207* (2013.01)

(58) Field of Classification Search
None
See application file for complete search history.

(56) References Cited

U.S. PATENT DOCUMENTS 5,403,322 A * 4/1995 Herzenberg ......... A61B 17/171 606/98

* cited by examiner

*Primary Examiner* — Sameh Boles
(74) *Attorney, Agent, or Firm* — Dennis A. DeBoo; Audrey A. Millemann; Weintraub Tobin

(57) ABSTRACT

A system comprised of custom radiographically designed tibial and talar cutting guides, a tibial reaming guide and bit, and instrumentalities for use in total ankle replacement surgery and a computer-based system and method for making the custom radiographically designed tibial and talar cutting guides.

12 Claims, 27 Drawing Sheets

In one embodiment of the invention, a method for manufacturing the custom tibial and talar cutting guides comprises the steps of:

1) Obtaining radiographic data of an ankle of a patient prior to undergoing total ankle replacement surgery;

2) Transforming the radiographic data into a virtual 3-dimensional model of the ankle for obtaining both tibial guide data correlative to a virtual 3-dimensional copy or model of a topography of an anterior surface portion of the distal tibia and talar guide data correlative to a virtual 3-dimensional copy or model of a topography of dome and dorsum surfaces of the talus;

3) Controlling a computer or numerical controlled machine system as a function of the tibial guide data for forming a custom radiographically designed tibial cutting guide comprised of a posterior surface having a first posterior surface portion with a topography that is an inversion or negative of an anterior surface portion of a distal tibia bone bordering three sides of a trapezoidal section of the tibia bone that is to be surgically removed during the total ankle replacement surgery; having a second posterior surface portion trapezoidally shaped and anteriorly depressed relative to the first posterior surface portion for defining a trapezoidally shaped posterior notch in the tibial cutting guide for receiving a tibial reaming guide circumscribing a reamer bit and locating the reamer bit along a central axis of the tibia for use in reaming a blind bore in the tibia along the central axis, and having cutting slits in the guide that borders the trapezoidal shaped second posterior surface for providing guided passage of a saw blade to make a superior tibial cut transversely, a lateral tibial cut, and a medial malleolus cut; and 4) Controlling a computer or numerical controlled machine system as a function of the talar guide data for forming a custom radiographically designed talar cutting guide comprised of a dome member having a inferior surface which is an inversion or negative of a dome surface portion of the talus and a neck member having a posterior surface which is an inversion of a dorsum surface portion of the talus; and having a cutting slit in the neck member for providing guided passage of a saw blade to make a talar or dome cut transversely.

FIG. 9

CUSTOM RADIOGRAPHICALLY DESIGNED CUTTING GUIDES AND INSTRUMENTS FOR USE IN TOTAL ANKLE REPLACEMENT SURGERY

CROSS-REFERENCE TO RELATED APPLICATIONS

This application is a continuation patent application of U.S. patent application Ser. No. 12/798,417, filed Apr. 2, 2010, currently pending and which claims priority under 35 USC Section 119(e) to U.S. Provisional Patent Application No. 61/212,533, filed Apr. 13, 2009 and to U.S. Provisional Application No. 61/270,203, filed Jul. 06, 2009, all three disclosures of which are incorporated herein by reference in their entireties.

FIELD OF THE INVENTION

This invention relates generally to a system for use in total ankle replacement surgery, and, in particular, to a system comprised of custom radiographically designed cutting guides and instruments for use in total ankle replacement surgery.

BACKGROUND OF THE INVENTION

Total joint replacement is an orthopedic technique in which the diseased ends of bone at a joint are removed and replaced by a combination of metal and plastic prostheses. Joint replacement surgery is done to relieve pain and retain motion of the joint. Total joint replacement is very successful in the larger joints of the lower extremity, the hip and knee. Recently, new techniques and prosthetic designs have made this procedure more common as a treatment option for ankle arthritis.

During total joint replacement surgery precise cuts are made in the ends of the bones by the joint to remove the diseased joint surfaces. A metal appliance, or prosthesis, is then applied on the end of each bone, with a plastic spacer between them. Each joint has its own unique anatomy and functional characteristics. Different prosthetic designs require bone cuts with unique geometry. For the ultimate joint function to be optimal, bone cuts must be accurate so that the prostheses are placed in the proper alignment and orientation.

Currently, there are several designs of total ankle replacement prostheses. One type of total ankle replacement prosthesis is sold by Wright Medical Technology, Inc. (5677 Airline Road, Arlington, Tenn. 38002, USA) under the trademark INBONE Total Ankle System. The INBONE Total Ankle System includes a large intramedullary stem on the tibial side. Although the existing technique used to define the bone cuts for this prosthesis can be accurate, it is very complex thereby rendering it problematic to work with. Specifically, the existing technique or defined algorithm that is used during surgery to determine the alignment and position of cuts in the bone for the correct insertion of this prosthesis is as follows.

First, the anterior ankle is exposed through a longitudinal incision. The leg, ankle and foot are then placed into a leg-holding frame, with the ankle in neutral dorsiflexion and plantarflexion.

The leg is manipulated under fluoroscopy to show a true mortise view. The mortise view is a standard radiographic description of an internally rotated view of the ankle that looks down the axis of the body of the talus between the medial and lateral malleolei. The x-ray beam is perpendicular to the intermalleolar axis. In this situation the intermalleolar axis is parallel to the top of the operating table. Once this position is established, it is maintained by fixing the foot into the leg holder frame with K-wires drilled through the frame and into the heel.

The long axis of the tibia is then determined using guide rods built into the leg holder frame. Sets of guide rods in the anterior-posterior and medial-lateral planes are manipulated using fluoroscopy to align the long axis of the tibia with the leg holder.

After an incision is made in the bottom of the heel, a drill guide built into the leg holder frame is placed against the undersurface of the calcaneus. The frame and alignment rods are designed to position the drill guide along the central axis of the tibia. A drill bit is used to make a Channel up through the calcaneus and talus, and into the distal tibia. This drill bit follows the central axis of the tibia, established by the alignment of the drill guide built into the leg holder frame.

The size of the implants to be used is based on the size of the ankle bones seen on the fluoroscopy views. There are 5 sizes of implant sets and a saw guide that corresponds to each size. Each set of implants comprises a tibial implant, a talar implant and a polyethylene spacer.

The tibial implant is constructed from different components. The inferior part is a tibial tray. This has a set size and morphology specified by the size of the implant set chosen. Superior to this is a base, which also has a set size and morphology specified by the size of the implant set chosen. Superior to this are a variable number and size of stem components that are chosen by the surgeon during the procedure to give the best fit in the tibial intramedullary canal.

The talar component has a set size and morphology specified by the size of the implant set chosen. There is a stem that fits into the inferior portion of the talar implant and extends inferiorly either 10 mm or 14 mm at a defined angle. The choice of which stein length to use is made by the surgeon during the procedure.

Each implant set has a defined number of polyethylene spacers of varying height that fit into the tibial tray on the tibial implant. The height of the spacer to be used is chosen by the surgeon during the procedure, after the tibial and talar components have been fit into the bones.

Additionally, each implant set has a saw guide that corresponds to the size of the implants. Each saw guide has four slits built into it that allow passage of a saw, and define the orientation of the bone cuts. A slit for a superior cut is made in the distal tibia. A parallel inferior cut is made in the superior talus defined by an inferior slit. Oblique medial and lateral cuts are made in the distal tibia and onto the superior talus with the two other slits. When viewed from anterior the guide defines a trapezoidal set of cuts in the ankle.

The saw guide fits into the top of the leg holder frame and can be moved about above the anterior surface of the ankle joint, and will superimpose with the ankle bones when viewed with fluoroscopy. The ankle is still held in the position that gives the mortise view. Using fluoroscopy, the center of the saw guide is aligned with the drill bit in the central axis of the tibia. It is positioned to make parallel superior and inferior cuts that take a similar depth of bone from the dorsum of the talus and inferior surface of the tibia. The medial cut into the medial malleolus should be less than ⅓ of the width of that segment of bone. The lateral cut should just come against the medial surface of the lateral malleolus without cutting into it. When viewed in the medial-lateral plane with fluoroscopy, the cuts should be perpendicular to the long axis of the tibia and the bottom of the foot. The size of saw guide that meets these parameters is then chosen. This determines the size of the implant set to be used.

Once the chosen size saw guide is properly positioned over the anterior ankle, it is stabilized with K-wires drilled through it and into the tibia and talus bones. Then a saw is used to make the tibial and talar cuts through the slits in the guide. The guide is removed and the cut bone segments are also taken out. This leaves a trapezoidal space between the bones into which the implant set will fit.

The distal tibia is then further prepared by reaming along its central axis to accommodate the proper size of the tibial stem. The diameter of the channel to be reamed is determined by the size of the stem to be used. To ream the tibia, the proper diameter bit is put into the ankle space through the anterior wound. A reamer driver is passed through the drill guide against the bottom of the calcaneus, and superiorly through the channel made by the drill bit into the ankle space to meet the reamer bit. After the driver engages the reamer bit, reaming along the central axis of the distal tibia is performed. The frame and guide ensure that the reaming is done with the proper alignment along the central axis.

The talus is finally reamed for the stem of the talar prosthetic component. The position for talar reaming is determined by a guide attached to the frame, and is based on the central axis of the tibia.

Although the above delineated technique is accurate, its complexity has disadvantages. For example, the frame that holds the leg must be constructed sterilely for each patient, a process that takes up valuable operating room time. Additionally, the process of determining the proper alignment of the ankle in the frame prior to cutting the bone is technically exacting, and also time-consuming. There is often a significant amount of fluoroscopic imaging required during the alignment process. Furthermore, all of the equipment used for this procedure must be processed for each separate use.

Another problem with this system, and with all of the existing systems for total ankle replacement, is difficulty in correcting angular deformities that are present. Most arthritis in the ankle is secondary to pre-existing trauma, and it is not uncommon for patients undergoing total ankle replacement to have malalignment at the ankle, or concurrent malalignment in the hindfoot. If an external frame is used to hold the leg, it maintains the relationship between the ankle bones, and the hindfoot, even if there is malalignment. Existing cutting guides used with these systems make both the tibial and talar bone cuts simultaneous with one saw guide. The cuts in the two bones are thus linked and are strictly dependent on the position of each bone relative to the other. Consequently, if an abnormal angular relationship exists between the two bones, it will be maintained after the bone cuts have been made.

Moreover, techniques have been developed to make custom bone cutting guides for knee joint replacement surgery. In those techniques, preoperative CAT scan or MRI scans are analyzed, and plastic models fabricated to fit against surfaces of the bones at the knee. Those plastic guides have appropriate slits placed in them that define the position that a saw blade can be inserted against the bone. The placement of those slits in the guides is made based on an analysis of the morphology of the bones and joint for the particular patient, combined with an understanding of the size and shape of the particular artificial joint prosthesis that will be used.

Accordingly, there is a need for a system for use in total ankle replacement surgery that overcomes the significant shortcomings of the known prior-art as delineated hereinabove.

BRIEF SUMMARY OF THE INVENTION

Accordingly, and in one aspect, an embodiment of the invention ameliorates or overcomes one or more of the significant shortcomings of the known prior art by providing a system comprised of custom guides defined by preoperative CAT scan or MRI scan analysis and a set of instrumentalities for use with the custom guides. In one aspect, the system improves the precision of bone cuts, eliminates the need for a large external frame to hold the ankle immobile, simplifies the operative procedure, decreases the operative time, minimizes the need for intra-operative fluoroscopy and allows better correction of deformities by independent bone cuts and reaming of the tibia and talus bones.

One important difference between the ankle and knee for joint replacement surgery is the exposure of the bones for cutting and reaming. During joint replacement surgery for each an anterior longitudinal incision is made to expose the bones at the joint. For the knee, this approach leads to the convex side of the joint. This places the ends of the bones external to the skin, a position that makes them easily accessible for the cutting guides. For the ankle, the anterior approach leads to the concave side of the joint. The ends of the bones thus remain interior as they are being prepared during the surgery. Hence, different types of instruments must therefore be used when performing ankle joint replacement surgery.

More particularly, and in one aspect, an embodiment of the invention provides a custom radiographically designed cutting guide system for use in total ankle replacement surgery, the system comprising: a tibial cutting guide having a first posterior surface portion with a topography that is a preoperatively defined negative of an anterior topography of a distal portion of a tibia of a patient to fit the first posterior surface portion of the tibial cutting guide to the distal portion of the tibia in one unique position; the tibial cutting guide having a second posterior surface portion anteriorly recessed from the first posterior surface portion at a preoperatively defined distance from a central longitudinal axis of the tibia for defining a tibial reaming guide locator notch anteriorly recessed from the first posterior surface portion; and the tibial cutting guide having at least one slit to guide a cutting instrument to make at least one cut in the distal portion of the tibia of the patient with the tibial cutting guide in the one unique position wherein at least the one cut is in a boundary of a segment of the distal portion of the tibia to resect during total ankle replacement surgery.

Additionally, an embodiment of the invention provides a computer-based method for making the custom radiographically designed tibial cutting guide.

In another aspect, an embodiment of the invention provides a custom radiographically designed cutting guide system for use in total ankle replacement surgery, the system comprising: a talar cutting guide comprised of a dome member and a neck member; the dome member having an inferior surface portion with a topography that is a preoperatively defined negative of a topography of at least a portion of a dome surface of a dome of a talus of a patient to fit the inferior surface portion of the dome member to at least the portion of the dome surface of the dome of the talus in one unique position; and the neck member having a posterior surface portion with a topography that is a preoperatively defined negative of a topography of at least a portion of a dorsum surface of a talar neck of the talus to fit the posterior surface portion of the neck member to at least the portion of the dorsum surface of the talar neck of the talus in one unique position.

Additionally, an embodiment of the invention provides a computer-based method for making the custom radiographically designed talar cutting guide.

In further aspect, an embodiment of the invention provides a custom radiographically designed cutting guide system for use in total ankle replacement surgery, the system comprising: a tibial reaming guide sized to fit in a space formed by a resected segment of a distal portion of a tibia and a resected segment of a dome of a talus, the tibial reaming guide having a opened ended channel; a cannulated reaming bit removably received within the opened ended channel of the tibial reaming guide; and the cannulated reaming bit having a hone reaming exterior surface for forming a bore in the tibia when driven wherein the bore is sized to receive an intramedullary stem of a preoperatively chosen total ankle prosthesis.

Accordingly, having thus summarized the invention, it should be apparent that numerous modifications and adaptations may be resorted to without departing from the scope and fair meaning of the present invention as set forth hereinbelow by the claims.

BRIEF DESCRIPTION OF THE DRAWINGS

FIG. 9 is a general flowchart view of an embodiment of a method for producing the custom tibial cutting guide and the custom talar cutting guide with a manufacturing system generally presented in the block diagram illustrated in FIG. 8.

DETAILED DESCRIPTION OF THE INVENTION

Figure 1:
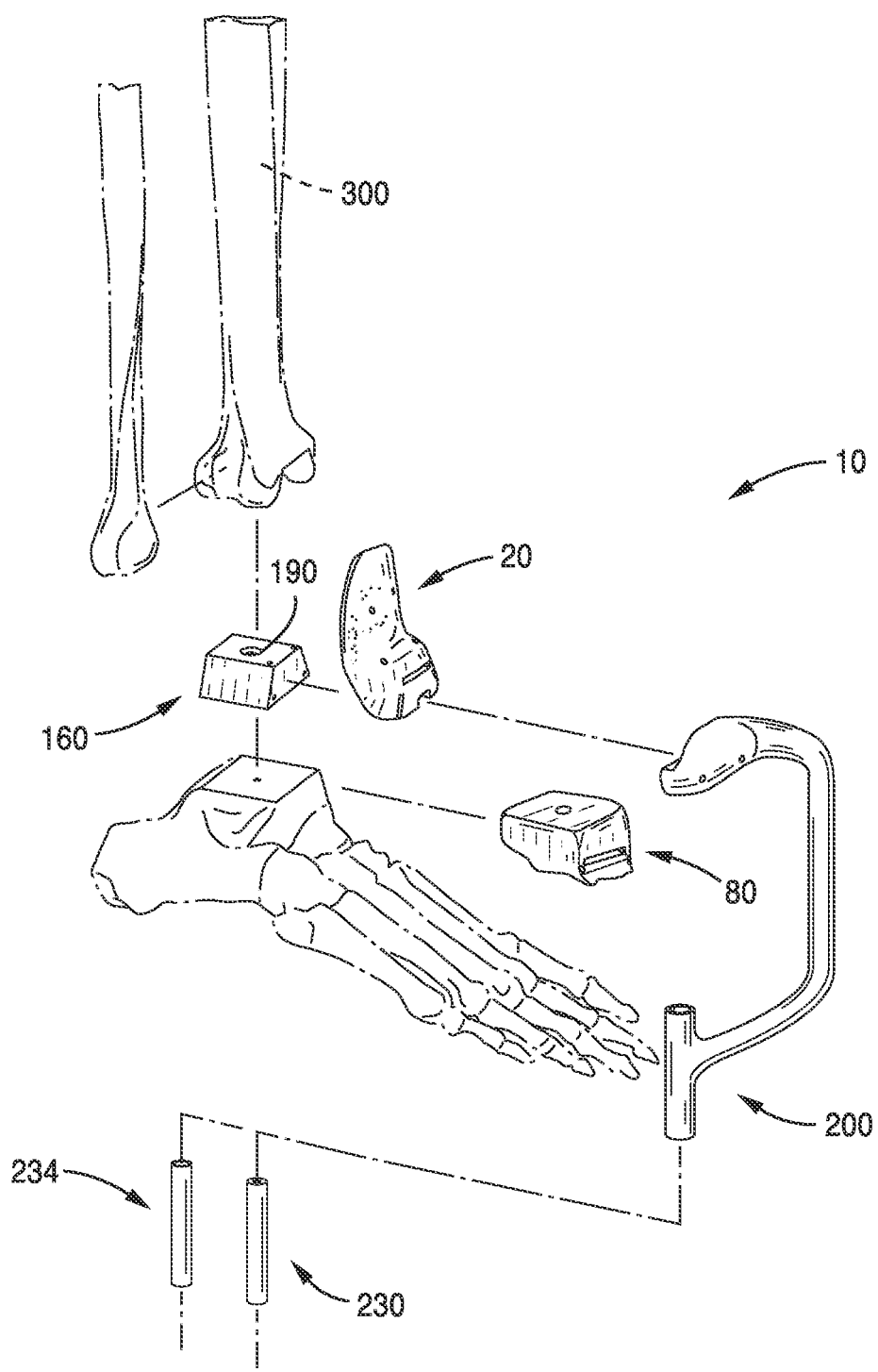
FIG. 1 is a front and side perspective view of a system for use in total ankle replacement surgery, the system comprising a custom tibial cutting guide, a custom talar cutting guide, a tibial reaming guide circumscribing a removable, cannulated reaming bit, a C-shaped outrigger alignment guide, a cylindrically shaped inner sleeve wire guide, and a cylindrically shaped inner sleeve drill and driver bit guide, and further illustrating a fragmentary front and side perspective view of a human leg and foot illustrating an ankle joint comprised of a fibula and a prepared tibia of the leg, and a prepared talus of the top of the foot.

Considering the drawings, wherein like reference numerals denote like parts throughout the various drawing figures, reference numeral 10 is directed to a system for use in total ankle replacement surgery.

Referring to FIG. 1, and in one embodiment, the system 10 is comprised of a set of two patient-specific, radiographically designed, custom-made cutting guides: a custom tibial cutting guide 20 and a custom talar cutting guide 80. Additionally, the system 10 is comprised of a tibial reaming guide 160 circumscribing and aligning a removable, cannulated reaming bit 190. The system 10 is further comprised of a C-shaped outrigger alignment guide 200 that receives two removable, alternate inner sleeve guides: a cylindrically shaped inner sleeve wire guide 230 and a cylindrically shaped inner sleeve drill and driver bit guide 234. Moreover, and referring to FIGS. 15 and 17, the system 10 is comprised of a skeleton cage or first frame member 240 and a double fork cage or second frame member 260 for use during prosthesis placement.

Custom Tibial Cutting Guide 20

Figure 2:
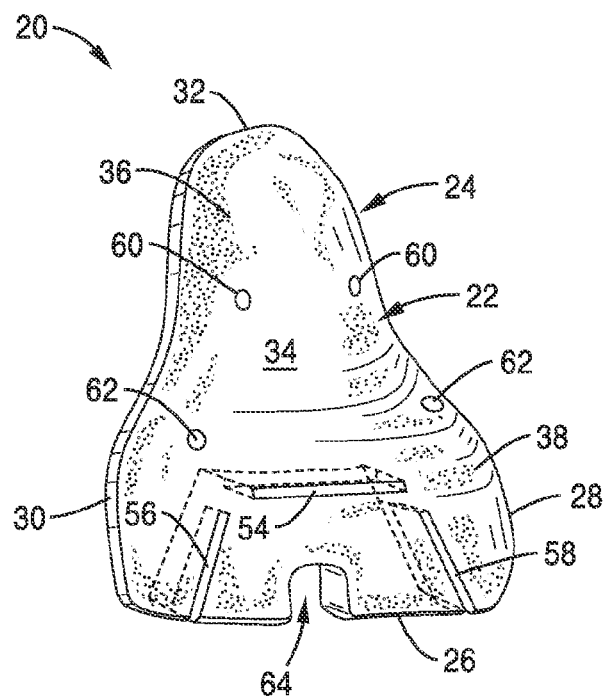
FIG. 2. is a front perspective view of a custom tibial cutting guide illustrating bone fixation holes, tibial reaming guide alignment holes, saw cutting slits, and an outrigger alignment guide keyway notch.

More specifically, and referring to FIGS. 1 and 2, the custom tibial cutting guide 20 is comprised of a generally half-bell-shaped body 22 having a generally bell-shaped peripheral edge 24.

The generally bell-shaped peripheral edge 24 is comprised of a generally flat distal edge 26 transitioning at one end to a proximally extending, curved shaped inner edge 28 and transitioning at the other end to a proximally extending, curved shaped outer edge 30. The generally bell-shaped peripheral edge 24 is further comprised of a rounded proximal edge 32 bridging the proximal ends of the inner and outer edges 28, 30 together.

The "half-bell-shape" as used herein refers to a general shape of a bell having an outwardly flaring opening and bisected by a plain parallel to the bell's longitudinal axis.

The generally half-bell-shaped body 22 is comprised of an anterior surface 34 circumscribed by the generally bell-shaped peripheral edge 24. The anterior surface 34 is comprised of a proximally tapered convex anterior surface portion 36 integrally formed with a distally flared bulbous anterior surface portion 38. The proximally tapered convex anterior surface portion 36 distally extends from the rounded proximal edge 32 while widening and then transitioning into the distally flared bulbous anterior surface portion 38 which terminates into the generally flat distal edge 26.

Figure 3:
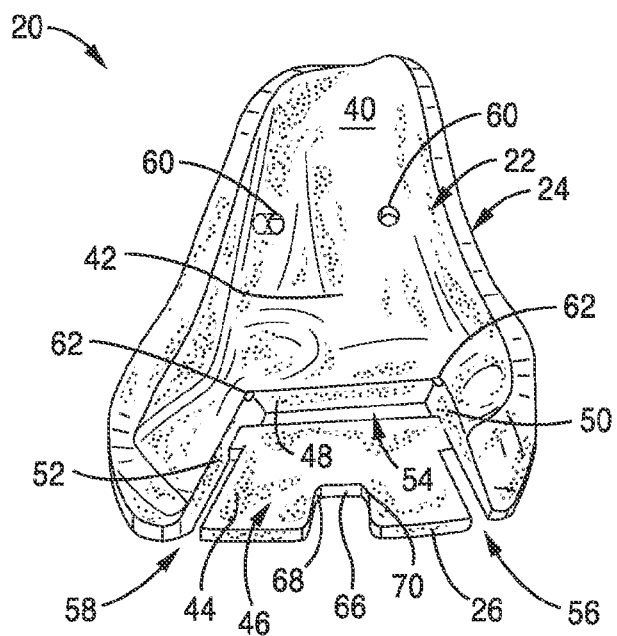
FIG. 3 is a back perspective view of the custom tibial cutting guide illustrating bone fixation holes, tibial reaming guide alignment holes, saw cutting slits, the outrigger alignment guide keyway notch, a reaming guide locator notch, and a posterior surface that has a patient specific topography that is a preoperatively defined negative or inversion of an anterior topography or surface of a distal portion of the patient's tibia.
Figure 4:
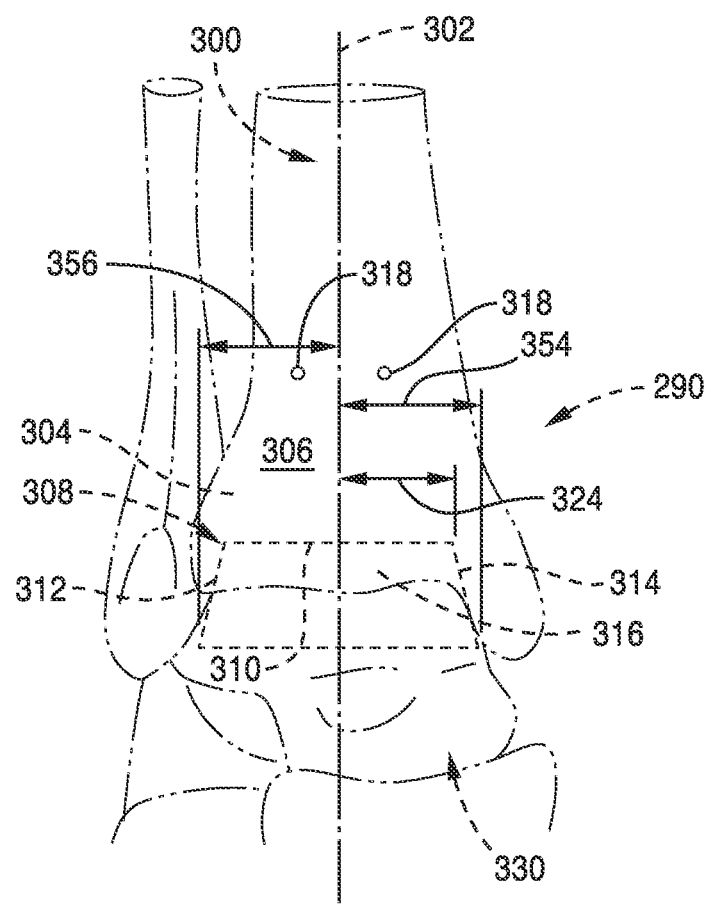
FIG. 4 is a fragmentary front elevational view of a human leg and foot illustrating an ankle joint comprised of a tibia and fibula bone of the leg, and a talus bone of the top of the foot and further illustrating a central axis of the distal tibia and a bone preparation area outlined by a broken line trapezoid.
Figure 5:
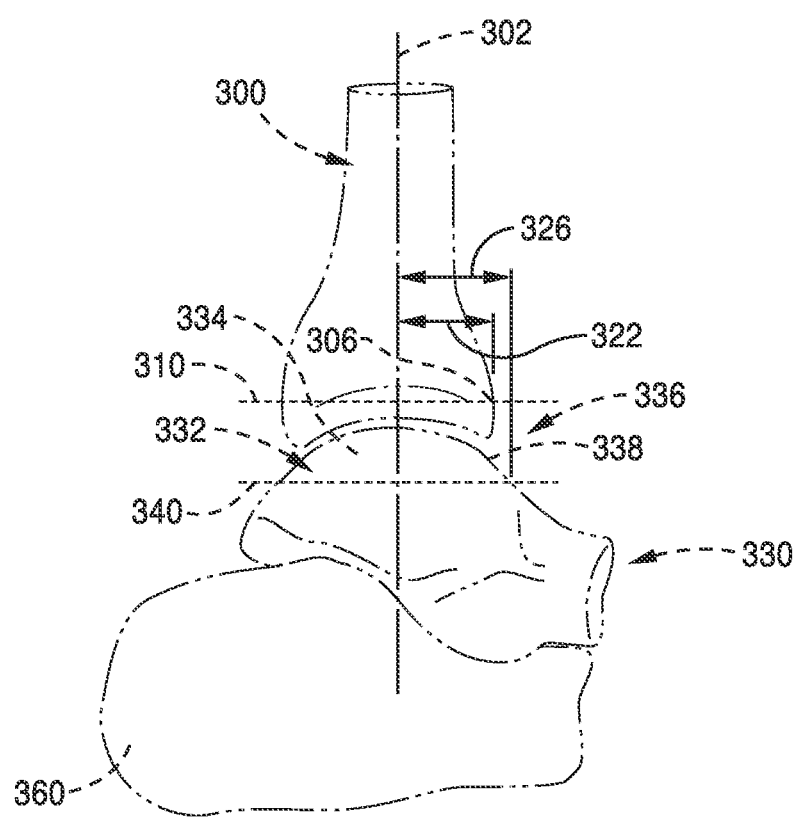
FIG. 5 is a fragmentary side elevational view of the tibia bone of the leg and the talus bone of the top of the foot and further illustrating the central axis of the distal tibia and illustrating, in broken lines, a central long axis of the distal tibia, a tibia bone cut location, and a talus bone cut location.

Additionally, and referring to FIGS. 3 through 5, the generally half-bell-shaped body 22 is comprised of a posterior surface 40 circumscribed by the generally bell-shaped peripheral edge 24. The posterior surface 40 is comprised of a first posterior surface portion 42 that has a topography that is a preoperatively defined inversion or negative of an anterior surface portion 306 of a distal portion 304 of a tibia 300 to which the custom tibial cutting guide 20 is fitted in one unique position during the total ankle replacement surgery. The first posterior surface portion 42 borders a superior base side and portions of two non-parallel sides of a broken line trapezoidal section 308 that outlines a trapezoidal portion of the tibia 300 and a talus 330 that is to be surgically removed or resected during the total ankle replacement surgery as will be further detailed below.

The posterior surface 40 of the body 22 is further comprised of a second posterior surface portion 44 that is trapezoidally shaped and anteriorly recessed relative to the first posterior surface portion 42 for defining a trapezoidally shaped posterior locator notch or reaming guide locator notch 46 in the custom tibial cutting guide 20. The reaming guide locator notch 46 is defined by the trapezoidally shaped second posterior surface portion 44, a superior base surface 48, an angled lateral or outer surface 50, and an angled medial or inner surface 52 wherein the superior base surface 48, angled lateral or outer surface 50, and angled medial or inner surface 52 generally extend perpendicularly between the first and second posterior surfaces 42, 44 of the custom tibial cutting guide 20. Accordingly, the reaming guide locator notch 46 extends between the generally flat distal edge 26 and the superior base surface 48, and between the angled outer and inner surfaces 50 and 52 thereby outlining the trapezoidal section 316 of the distal portion 304 of the tibia 300 that is surgically removed during the total ankle replacement surgery.

Figure 20:
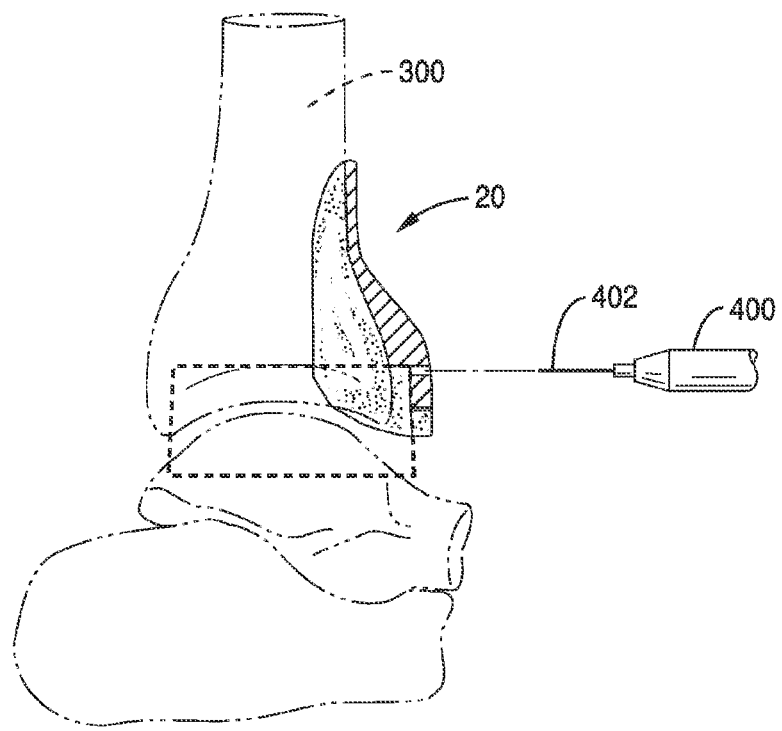
FIG. 20 is a side sectional view of the custom tibial cutting guide fit in place against the anterior surface of the distal tibia and further illustrating a tibia bone cut location in broken line and a conventional surgical saw and blade.
Figure 21:
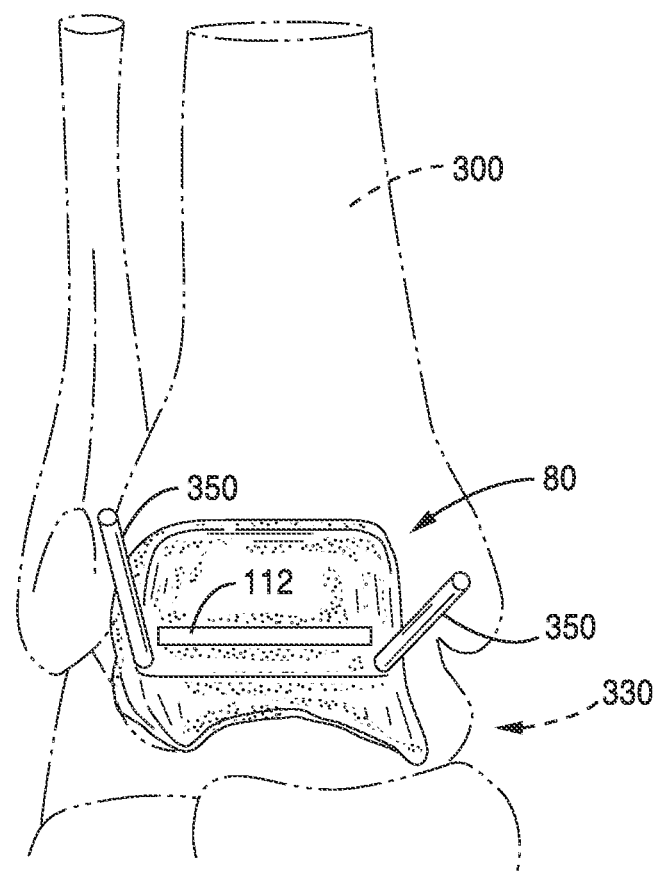
FIG. 21 is a front elevational view of the custom talar cutting guide shown fit in place against the superior surface of the dome of the talus and the anterior surface of the dorsum of the talar neck and removably secured thereto for use with a surgical saw and blade.
Figure 24:
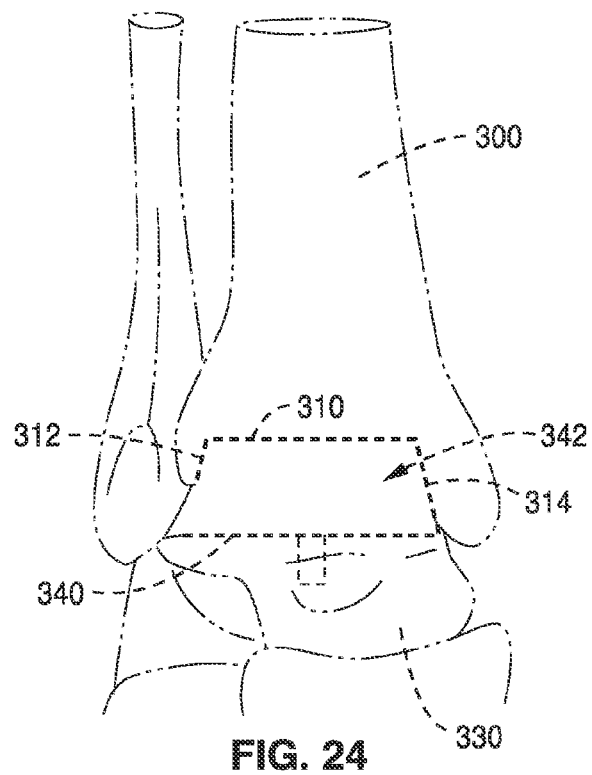
FIG. 24 is a fragmentary front elevational view of the ankle joint and further illustrating the tibia and talus bone cuts, the tibial-talar space, and the talar blind bore in broken line.

Additionally, the superior base surface 48 defines a superior base edge of a preoperatively located superior tibial cutting slit 54 disposed through the cutting guide 20 for guiding the passage of a saw blade 402 of a surgical saw 400 (FIG. 20) to make a superior tibial cut 310 transversely (FIGS. 4 and 24). The angled lateral surface 50 defines a lateral side edge of a preoperatively located lateral cutting slit 56 disposed through the cutting guide 20 for guiding the passage of the saw blade 402 to make the lateral tibial cut 312 (FIGS. 4 and 24). The angled medial surfaces 52 defines a medial side edge of a preoperatively located medial malleolus cutting slit 58 disposed through the cutting guide 20 for guiding the passage of the saw blade 402 to make the medial malleolus cut 314 (FIGS. 4 and 24) thereby defining three cutting zones of the distal portion 304 of tibia 300 for removing the trapezoidal section 316 of the distal portion 304 of the tibia 300 during the total ankle replacement surgery.

Figure 19:
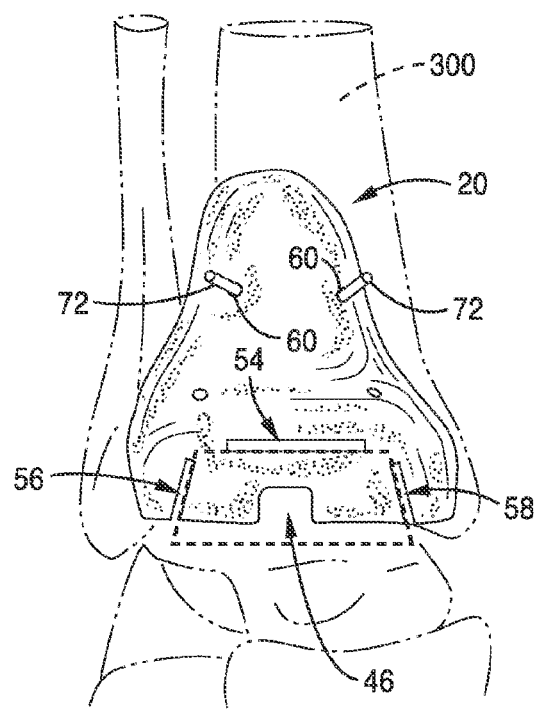
FIG. 19 is a front elevational view of the custom tibial cutting guide fit in place against the anterior surface of the distal portion of the tibia or the distal tibia and removably secured thereto.
Figure 25:
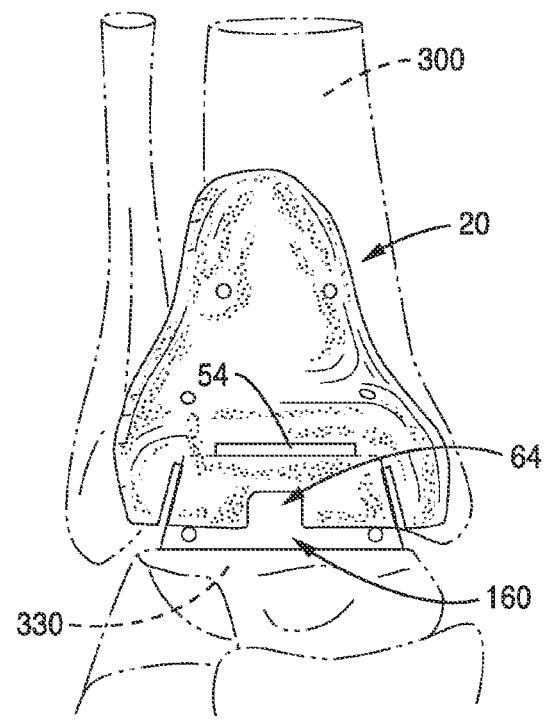
FIG. 25 is a front elevational view of the custom tibial cutting guide fit in place against the anterior surface of the distal tibia and fitted with the tibial reaming guide.

Furthermore, and referring to FIGS. 2 and 3, the custom tibial cutting guide 20 is comprised of a plurality of bone fixation holes 60 and reaming guide fixation holes 62. In one embodiment, two spaced apart bone fixation holes 60 pass through the generally half-bell-shaped body 22 of the custom tibial cutting guide 20 from the proximally tapered convex anterior surface portion 36 to the first posterior surface portion 42 for placement of wires or screws for the temporary fixation (FIG. 19) of the custom tibial cutting guide 20 to the distal portion 304 of the tibia 300 via tibia holes 318 (FIG. 4). Additionally, and in one embodiment, two spaced apart reaming guide fixation holes 62 pass through the generally half-bell-shaped body 22 of the custom tibial cutting guide 20 from the distally flared bulbous anterior surface portion 38 to the superior base surface 48 for placement of wires or screws for the temporary fixation of the tibial reaming guide 160 via holes 180 (FIGS. 10 and 25) into the reaming guide locator notch 46 of the custom tibial cutting guide 20 as will be further detailed below.

Moreover, and referring to FIGS. 2 and 3, the custom tibial cutting guide 20 is comprised of a preoperatively placed outrigger alignment guide locator notch 64 disposed through the generally half-bell-shaped body 22 of the custom tibial cutting guide 20. The outrigger alignment guide locator notch 64 extends from the distally flared bulbous anterior surface portion 38 to the trapezoidally shaped second posterior surface 44 while interrupting the generally flat distal edge 26. In one embodiment, the outrigger alignment guide locator notch 64 is defined by three outrigger guide locator notch surfaces: a superior notch surface 66, an inner notch surface 68, and outer notch surface 70 wherein the inner notch surface 68 generally normally depends distally from one end of the superior notch surface 66 while the outer notch surface 70 generally normally depends distally from the other end of the superior notch surface 66. In one embodiment, the outrigger alignment guide locator notch 64 is parallel to a central axis 302 of the tibia 300.

Custom Talar Cutting Guide 80

Figure 6:
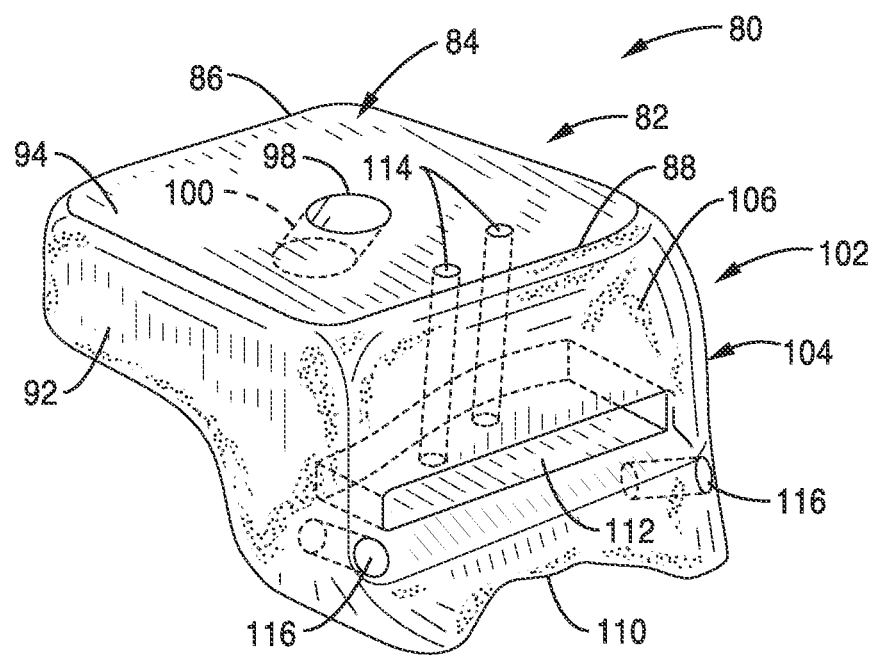
FIG. 6 is a top, front, and side perspective view of a custom talar cutting guide illustrating bone fixation holes, a saw cutting slit, and an angled reaming channel.
Figure 7:
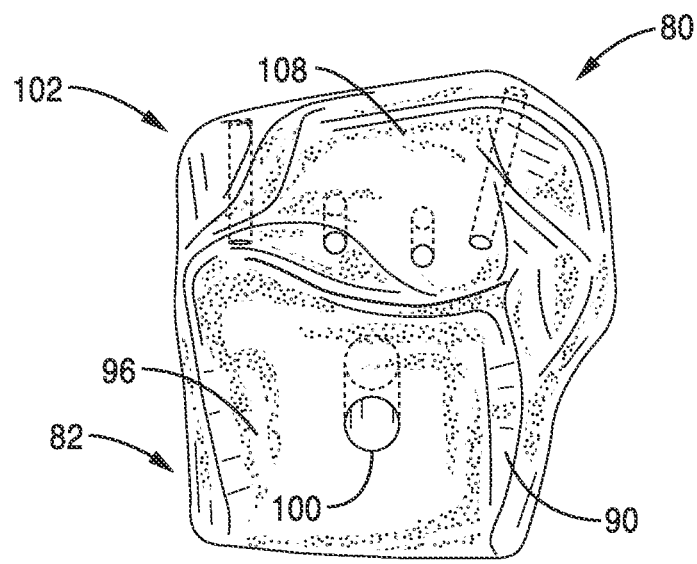
FIG. 7 is a bottom and back perspective view of the custom talar cutting guide illustrating an inferior surface and a posterior surface of the talar custom cutting guide that have patient specific topography that are, respectively, a preoperatively defined negative or inversion of a topography of a dome of the patient's talus and of a topography of a dorsum of a talar neck of the patient's talus and further illustrating the bone fixation holes and the angled reaming channel.

Referring to FIGS. 6 and 7, the custom talar cutting guide 80 is generally L-shaped in configuration and is comprised of a dome member 82 and a neck member 102 integrally formed therewith.

The dome member 82 is comprised of a generally rectangularly shaped body 84 longitudinally extending between a posterior end 86 and an anterior end 88 and laterally extending between a distally extending inner sidewall 90 and a distally extending outer sidewall 92. Additionally, the generally rectangularly shaped body 84 includes a superior or upper surface 94 and inferior or lower surface 96. The superior or upper surface 94 is generally flat and the inferior or lower surface 96 has a topography that is a preoperatively defined inversion or negative of the topography of a dome surface 334 of a dome 332 of a talus 330 (FIG. 5) on which it is mounted during the total ankle replacement surgery.

The generally rectangularly shaped body 84 is further comprised of an open ended, angled reaming channel or bore 98 that is disposed through the body 84 at a preoperatively defined location and at a preoperatively defined angle. The angled reaming channel or bore 98 is defined by a cylindrically shaped interior surface 100 that angularly extends posteriorly from the superior surface 94 to the inferior surface 96 at the preoperatively defined angle.

The neck member 102 is integrally formed with and distally depends from the anterior end 88 of the dome member 82. The neck member 102 is comprised of a generally rectangularly shaped body 104 comprised of an anterior or outer surface 106 and a posterior or inner surface 108. The anterior surface 106 of the neck member 102 generally perpendicularly extends distally from the superior surface 94 of the dome member 82, The posterior surface 108 of the neck member 102 comprises a topography that is a preoperatively defined inversion or negative of topography of a dorsum surface 338 of a talar neck 336 of the talus 330 (FIG. 5) to which it is to be received. The anterior and posterior surfaces 106, 108 distally terminate to a distal end surface 110 having a topography that is a preoperatively defined inversion or negative of the topography of a portion of the dorsum surface 338 of a talar neck 336 of the talus 330 on which it is fitted.

Additionally, the neck member 102 is comprised of a preoperatively sized and located talus cutting slit 112 disposed therethrough to guide the passage of a saw blade 406 powered by a surgical saw 400 (FIG. 22) for cutting the top of the talus along the talus cut line 340 (FIG. 5) during the total ankle replacement surgery.

Furthermore, the neck member 102 is comprised of a plurality of dome fixation holes 114 and neck fixation holes 116 as illustrated in FIG. 6. In one embodiment, two spaced apart dome fixation holes 114 pass through the superior surface 94 of the dome member 82 and pass through the generally rectangularly shaped body 104 of the neck member 102 at a location superior to the cutting slit 112 for allowing placement of wires or screws 346 for temporary fixation into the dome 332 via holes 348 (FIG. 23).

Figure 23:
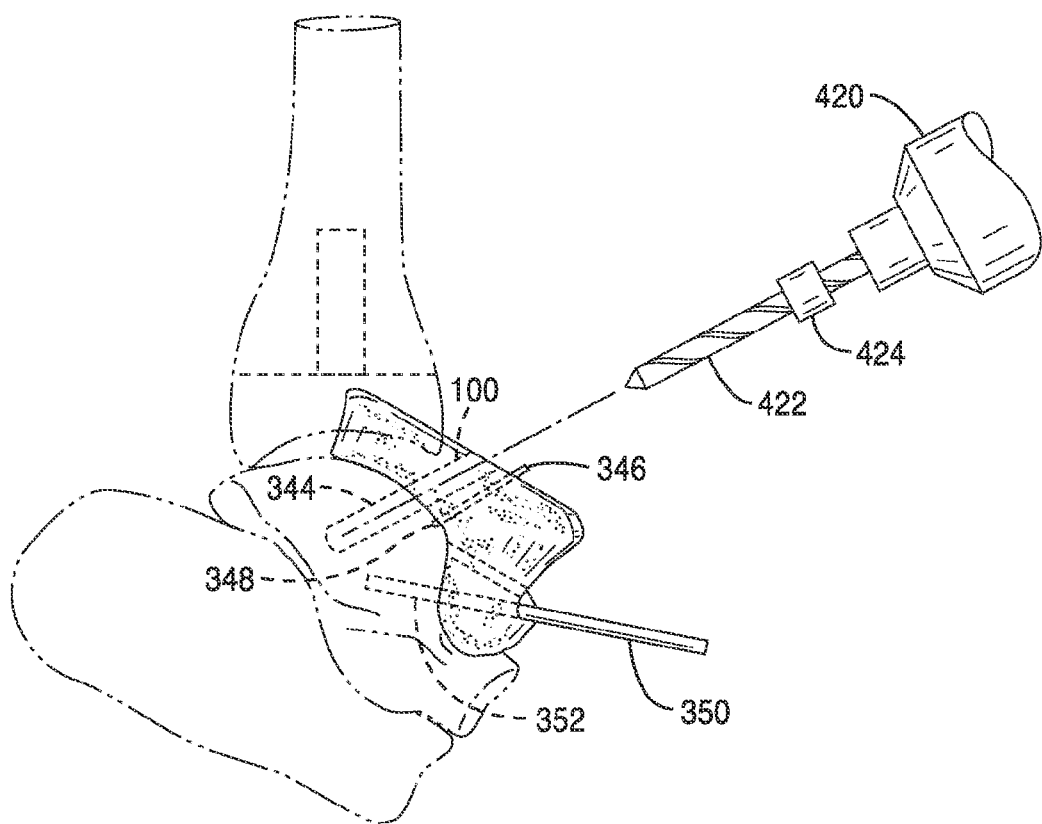
FIG. 23 is a side elevational view of the custom talar cutting guide shown fit in place against the superior surface of the dome of the talus and the anterior surface of the dorsum of the talar neck and removably secured thereto, and further illustrating the talar bone blind bore location in broken line and a conventional surgical drill and bit.

Additionally, and in one embodiment, two spaced apart neck fixation holes 116 pass through the generally rectangularly shaped body 104 of the neck member 102 at a location inferior to the cutting slit 112 for allowing placement of wires or screws 350 for temporary fixation into the dome 332 via holes 352 (FIG. 23).

System and Method for Manufacturing Custom Guides 20 and 80

Figure 8:
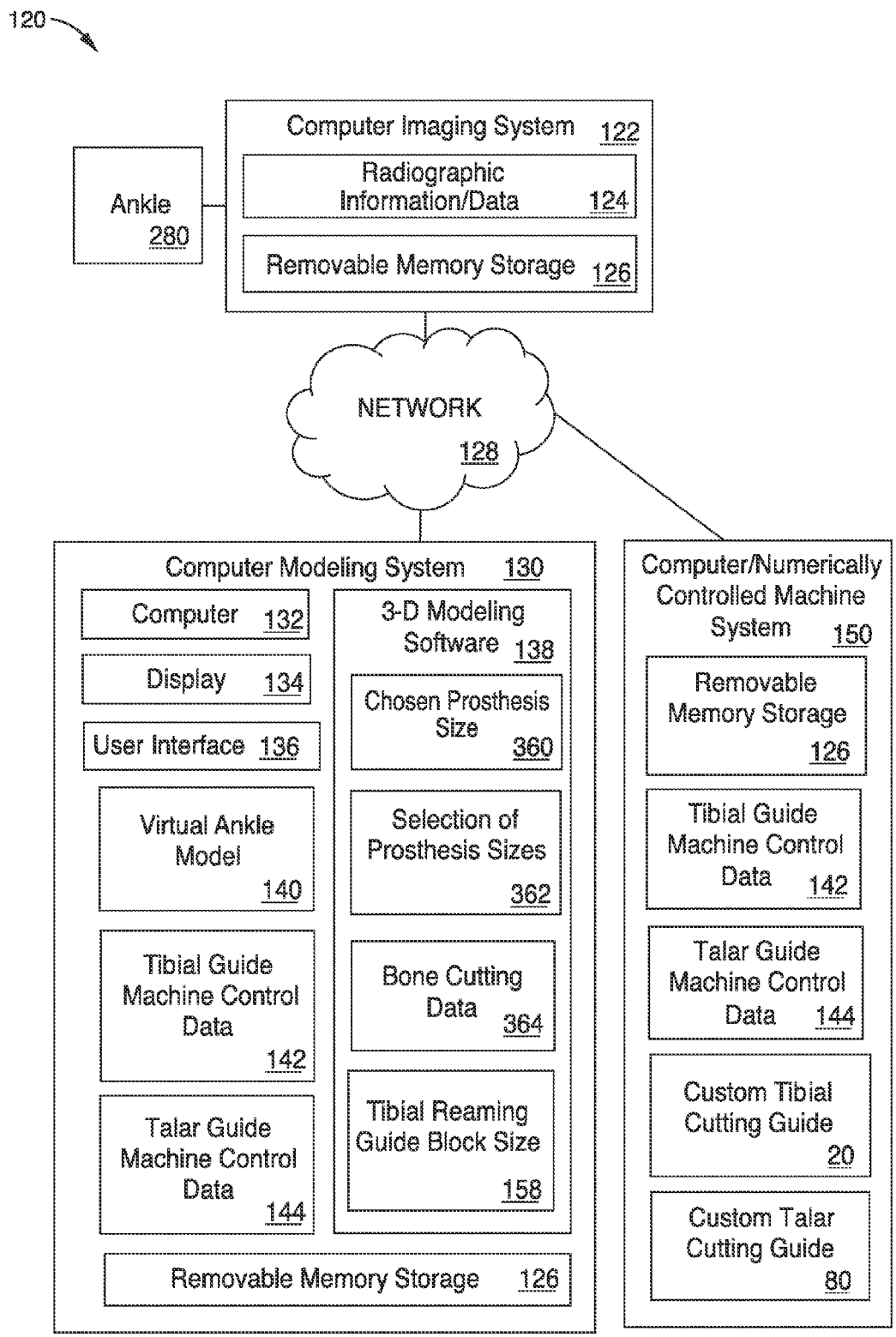
FIG. 8 is a general block diagram of a manufacturing system for producing the custom tibial cutting guide and the custom talar cutting guide.

In one embodiment, FIG. 8 illustrates a general block diagram of a manufacturing system 120 for producing the custom tibial cutting guide 20 and the custom talar cutting guide 80 in accordance with a method described below and generally illustrated via flow chart in FIG. 9.

Referring to FIG. 8, the system 120 is comprised of a computer imaging system 122 such as a CAT and/or a MRI system for obtaining radiographic information or data 124 of the patient's ankle 290 (FIG. 4). Additionally, the system 120 is comprised of a computer modeling system 130 comprised of, for example, a computer 132 having a display 134, a user interface or input apparatus 136 such as a keyboard and mouse, and existing 3-D modeling software 138 configured to operate on the computer 132. Furthermore, the system 120 is comprised of a computer or numerically controlled machine system 150 for manufacturing the custom tibial and talar cutting guides 20, 80 by, for example, a molding and milling process.

In general, and prior to surgery, the morphology of the patient's ankle 290 being replaced is assessed radiographically using the computer imaging system 122 for obtaining radiographic information or data 124. This radiographic information or data is used to render a virtual 3-dimensional copy or model 140 of the ankle 290 with the existing 3-D modeling software 138 of the computer modeling system 130. The 3-D modeling software 138 then analyzes the virtual ankle model 140 and chooses one of a plurality of available sizes of existing prostheses (for example, prostheses 370 illustrated in FIG. 30) and determines where the bones should be cut and reamed as a function of the radiographical analysis of the ankle 290 and the chosen size of the prosthesis. Accordingly, existing considerations are used in choosing one of the plurality of available sizes of existing prostheses and in determining the associated bone cuts correlative to the chosen size of the prosthesis; however, instead of the analysis being done during the surgical procedure, it is done preoperatively by utilizing the radiographic information or data 124 obtained by the computer imaging system 122 and the analysis provided by the computer modeling system 130.

Figure 22:
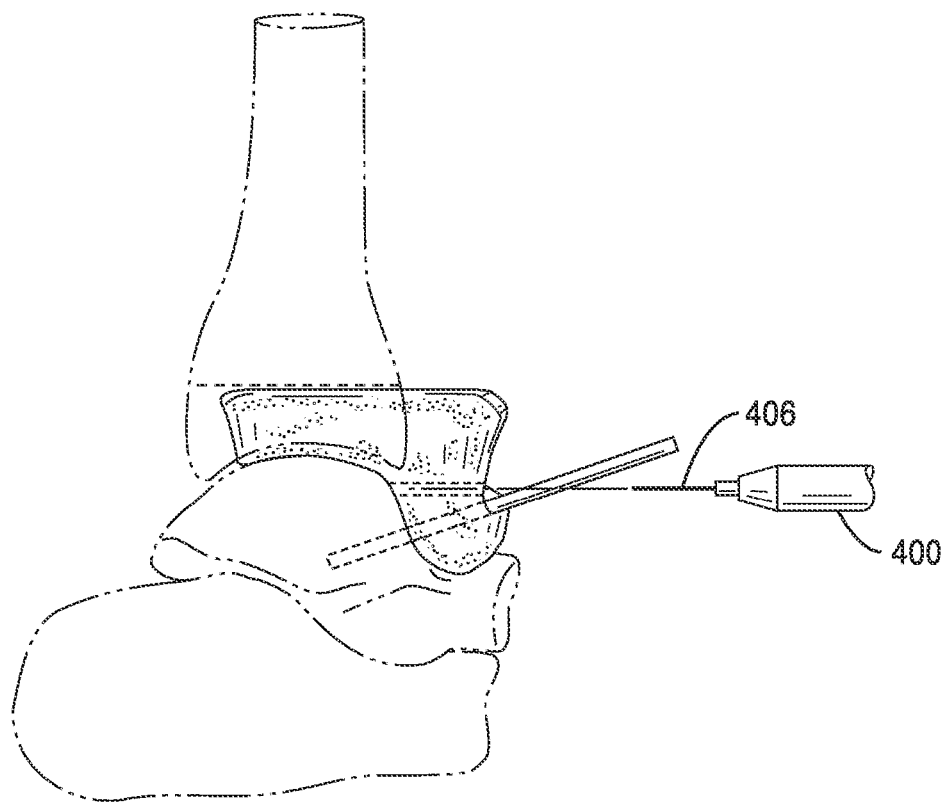
FIG. 22 is a side elevational view of the custom talar cutting guide shown fit in place against the superior surface of the dome of the talus and the anterior surface of the dorsum of the talar neck and removably secured thereto, and further illustrating a conventional surgical saw and blade for making the talar bone cut.

The computer or numerically controlled machine system 150 molds the custom tibial cutting guide 20 out of, for example, plastic and mills the guide 20 to fit precisely against the anterior border or surface portion 306 of the distal portion 304 of the tibia 300 (FIGS. 4, 19 and 20) as a function of tibial guide machine control data 142. Additionally, and as a function of talar guide machine control data 144, the computer or numerically controlled machine system 150 molds the custom talar cutting guide 80 out of, for example, plastic and mills the guide 80 to fit precisely on the dome surface 334 of the dome 332 of the talus 330 and against the dorsum surface 338 of the talar neck 336 of the talus 330 (FIGS. 5 and 22). Like a lock, the respective surfaces 42, 96, and 108 of the custom tibial and talar cutting guides 20, 80 match their respective bone surfaces in one unique position. Additionally, these plastic custom cutting guides 20, 80 are milled with precisely oriented slits that guide the position of saw blades, and holes for drill bits, reamer bits, and fixation pins or screws. When each guide 20, 80 is coupled to its respective bone in its unique position, the holes and slits are in the preoperatively determined position for each of them.

More specifically, and referring to FIGS. 8 and 9, an embodiment of a method for manufacturing the custom tibial cutting guide 20 and the custom talar cutting guide 80 comprises the following steps.

A step of operating the computer imaging system 122 for obtaining radiographic information or data 124 of the ankle 290 of the patient correlative to the morphology of the ankle 290 of the patient and prior to the patient undergoing total ankle replacement surgery.

A step of communicating the obtained radiographic information or data 124 from the computer imaging system 122 to the computer modeling system 130 via a removable memory storage medium 126 and/or via an interconnected network 128.

A step of utilizing the 3-D modeling software 138 for transforming the radiographic information or data 124 into a virtual 3-dimensional copy or model 140 of the ankle 290 and for analyzing and transforming the virtual 3-dimensional model 140 of the ankle as a function of known and computed criteria for obtaining tibial guide machine control data 142 and talar guide machine control data 144 for use in manufacturing the custom tibial and talar cutting guides 20, 80 thereby ultimately transforming the radiographic information or data 124 into the custom tibial and talar cutting guides 20, 80

In one embodiment, the known and computed criteria includes: choosing a proper prosthesis size 360 from a selection of prosthesis sizes 362 as a function of the virtual 3-dimensional ankle model 140. In one embodiment, the proper prosthesis size 360 is chosen from five different sizes of prosthesis currently available in the INBONE Total Ankle System wherein each size has an corresponding bone cutting guide template for use therewith and that is employed to define bone cutting data 364; determining the long central axis 302 (FIG. 4) of the tibia 300 of the patient as a function of the virtual 3-dimensional model 140 of the ankle 290; determining tibia and talar cut locations as a function of the chosen prosthesis size 360, the bone cutting data 364 correlative to the chosen prosthesis size, and the virtual 3-dimensional model 140 of the ankle 290 which includes utilizing the topography of the anterior border or surface 306 of the distal tibia 304 from the virtual 3-dimensional model 140 as a reference surface for the tibial cuts and utilizing the criteria that a plane of the superior tibial cut 310 (FIGS. 4 and 24) is substantially perpendicular to the central axis 302 of the tibia 300 and of a depth that is similar to the depth of the talar cut 340 (FIG. 5), that the medial malleolus cut 314 in the medial malleolus is no deeper than about one-third (⅓) of the interior depth of that bone, that an axis of the cut 314 (FIGS. 4 and 24) in the medial malleolus and the axis of the lateral cut 312 (FIGS. 4 and 24) of the tibia 300 each follow the "mortise"; that is, they are perpendicular to the intermalleolar axis thereby forming a trapezoidally shaped opening, and that the center of the axis of the cut 314 in the medial malleolus and the axis of the lateral cut 312 pass through the central axis of the tibia; determining a distance 322 (FIG. 5) defined as the distance from the central axis 302 of the tibia 300 to the anterior border or surface 306 of the distal portion 304 of the tibia 300 at the level of the superior tibial cut 310 and a distance 324 (FIG. 4) defined as the distance from the central axis 302 of the tibia 300 to the medial edge of the tibial cut at its superior surface wherein distance 322 and 324 define the position of the central axis 302 of the tibia 300 relative to the custom tibial cutting guide 20 on the anterior surface portion 306 of the distal portion 304 of the tibia 300; determining the depth of the reaming guide locator notch 46 formed in the posterior surface 40 of the custom tibial cutting guide 20 by utilizing the formula $D=D1-D2$ wherein $D=$the depth of the notch, D1 equals the distance from the central axis of the tibia to the anterior surface of the tibia (distance 322) at the superior tibial cut 310, and D2 equals the distance, parallel to the distance D1, from an anterior or front face 174 of a reamer body 162 of the tibial reaming guide 160 to the center of a channel 178 in the reamer body 162 (FIG. 10) and wherein the width of the locator notch 46 is determined by a predefined size 158 of the tibial reaming guide 160 corresponding to the chosen prosthesis 360 and determined by the computer modeling system 130; determining a location and depth of a blind bore 328 (FIG. 29) of the tibia 300 reamed along the central axis 302 of the tibia 300, the plane and parameters of the talar or dome cut 340 (FIGS. 4 and 24) of the talus 330, and a location, depth, and angularity of a reamed blind bore 344 (FIG. 23) of the talus 330 as a function of the chosen prosthesis size 360 and the virtual 3-dimensional ankle model 140 and by utilizing the criteria that the plane of the cut in the dorsum of the talus is parallel to the plane of the bottom of the foot, that the depth of this cut will be similar to the depth of the cut in the distal tibia 304, that a position of the dome of the talus and the central axis 302 of the tibia 300 are used to determine the placement of talar dome component 388 of a talar prosthesis component (FIG. 30) and the position of reaming for a stem 390 of the talar prosthesis component is referenced off the topography of the neck 336 of the talus 330 (FIG. 5), and wherein the width of the talus at the level of the cut equals distance 354 plus distance 356 and the position of the dome of the talus is determined by distances 326, 354, and 356 (FIGS. 4 and 5) which are utilized to determine the placement of the fixation holes 114, 116 in the custom talar cutting guide 80 (FIG. 6) wherein distance 326 is defined as the distance from the central axis 302 of the tibia 300 to the dorsum of the talar neck at the level of the of the cut 340 (FIG. 5) when the tibia and talus are properly aligned.

Accordingly, the analyses of the virtual 3-dimensional model 140 of the ankle 290 as a function of known and computed criteria results in the tibial guide machine control data 142 comprising information or data correlative to the anterior topography of the anterior surface 306 of the distal tibia 304 of the patient, the location and size of the tibia fixation holes 60, the location and size of the tibia saw cutting slits 54, 56, and 58, the location and size of tibial blind bore 328, the location and size of the tibial reaming guide locator notch 46, the location and size of the tibial reaming guide fixation holes 62, and the location and size of the outrigger alignment guide locator notch 64.

Additionally, the analyses of the virtual 3-dimensional ankle model 140 as a function of known and computed criteria results in the talar guide machine control data 144 comprising information or data correlative to information on the topography of the dome 332 of the talus 330 or the topography of dome surface 334 and the topography of the dorsum of the talar neck 336 or the topography of dorsum surface 338; the location and size of the fixation holes 114, 116; the location and size of the talus cutting slit 112; and the size, location, and angularity of the angled reaming channel or bore 100.

After obtaining tibial guide machine control data 142 and talar guide machine control data 144, the system 120 performs a step of communicating the tibial guide machine control data 142 and the talar guide machine control data 144 to the computer or numerically controlled machine system 150 via the interconnected network 128 and/or the removable memory storage medium 126.

Figure 30:
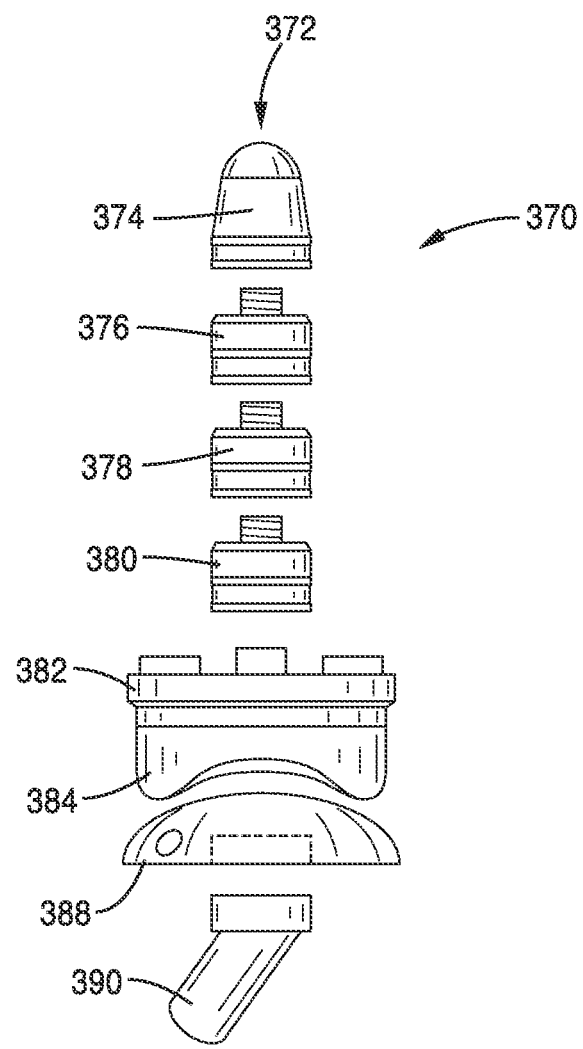
FIG. 30 is an exploded parts view of one size of one embodiment of the ankle prosthesis.

And, a further step of utilizing the computer or numerically controlled machine system 150 as a function of the tibial guide machine control data 142 and the talar guide machine control data 144 for respectively molding and milling the custom tibial cutting guide 20 and the custom talar cutting guide 80. As a result of the above utilizing step, the molded and milled custom tibial cutting guide 20 is comprised of the first posterior surface portion 42 which is the inversion of the anterior topography or surface 306 of the distal tibia 304, the reaming guide locator notch 46, the saw cutting slits 54, 56, 58, the tibia fixation holes 60, the reaming guide fixation holes 62, and the outrigger alignment guide locator notch 64 all precisely shaped, sized, and located as a function of the radiographic information or data 124 of the ankle 290 of the patient and the chosen size 360 of the prosthesis 370 (FIG. 30). Additionally, and a result of the above utilizing step, the molded and milled custom talar cutting guide 80 is comprised of the dome member 82 having the inferior surface 96 which is the inversion of the topography of the dome 332 of the talus 330 or of the topography of the dome surface 334; the angled reaming channel 100; the neck member 102 having the posterior surface 108 which is the inversion of the topography of the dorsum of the talar neck 336 or the topography of the dorsum surface 338; the talus cutting slit 112; and the talar fixation holes 114, 116 all precisely shaped, sized, and located as a function of the radiographic information or data 124 of the ankle 290 of the patient and the chosen size 360 of the prosthesis 370 (FIG. 30).

Tibial Reaming guide 160 and Cannulated Reaming Bit 190

Figure 10:
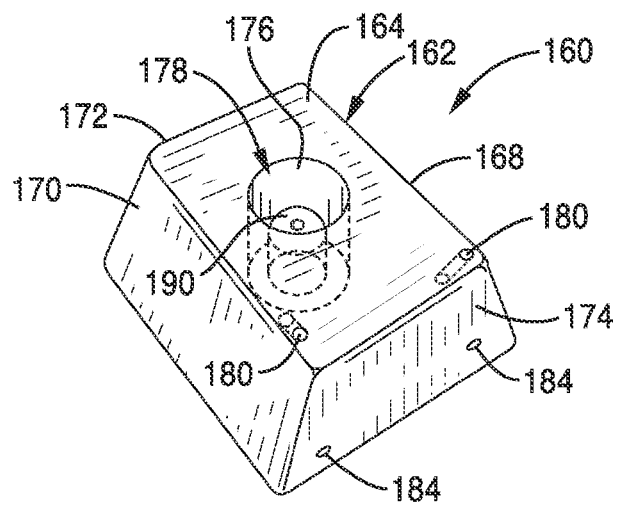
FIG. 10 is a top, front, and side perspective view of the tibial reaming guide having a central body channel circumscribing the removable, cannulated reaming bit, and further illustrating fixation holes fur removably attaching the tibial reaming guide to the custom tibial cutting guide and the C-shaped outrigger alignment guide.
Figure 11:
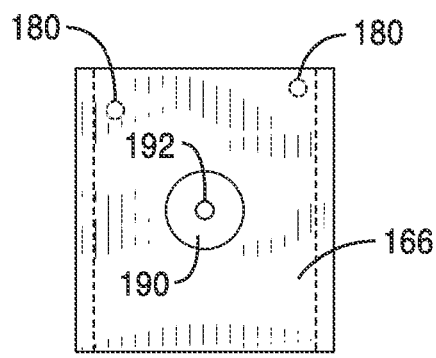
FIG. 11 is a bottom elevational view of the tibial reaming guide illustrated in FIG. 10.
Figure 12:
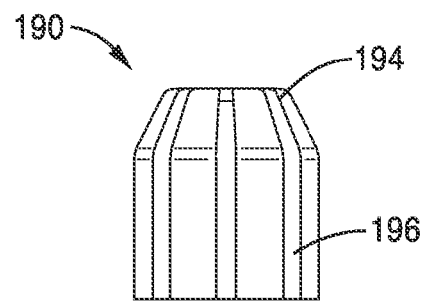
FIG. 12 is a side elevational view of the cannulated reaming bit.

Referring to FIGS. 10 through 12, and in one embodiment, the system 10 is further comprised of the tibial reaming guide 160 and the cannulated reaming bit 190 having a central opening or axial passage 192 for use in preparing the tibia 300 for an intramedullary stem that is in the form of a modular tibial stem component 372 of the chosen prosthesis 370 (FIG. 30). The tibial reaming guide 160 is designed come in a range of sizes that correspond to the different selection of prosthesis sizes 362.

In one embodiment, the tibial reaming guide 160 is comprised of a generally pyramidal frustum shaped reamer body 162 that is designed to fit into the tibial-talar space 342 defined as the space between the tibia 300 and the talus 330 after the resected tibial and talar bone segments have been removed. Accordingly, and as noted above, the reamer body 162 corresponds to the size of the chosen prosthesis 370 to be used, so if there are five different prosthesis sizes to choose from then there are five different tibial reaming guide sizes for providing a one to one correspondence between the two.

Referring to FIGS. 10 and 11, the generally pyramidal frustum shaped reamer body 162 is comprised of six faces: a superior face 164, an inferior face 166, an inner face 168, an outer face 170, a posterior face 172, and an anterior face 174. The superior and inferior faces 164 and 166 have a generally square or rectangular shape while the inner face 168, outer face 170, posterior face 172, and anterior face 174 have a generally trapezoidal shape. Additionally, the reamer body 162 of the tibial reaming guide 160 is comprised of an open ended, interior cylindrical surface 176 that defines an open ended cylindrically shaped central channel 178 that runs from the superior face 164 to inferior face 166 of the reamer body 162 and that is substantially perpendicular to those faces. The open ended cylindrically shaped central channel 178 receives the cannulated reaming bit 190 comprised of the axial passage 192 extending through the interior of the cannulated reaming bit 190 and a bone reaming exterior surface comprised of front cutting threads 194 and side cutting threads 196.

Furthermore, the generally pyramidal frustum shaped reamer body 162 has a central axis that passes through the center of the central channel 178 and that aligns or is coincident with the central axis 302 of the tibia 300 when the trapezoidally shaped anterior face 174 of the reamer body 162 abuts against the trapezoidally shaped posterior surface portion 44 of the reaming guide locator notch 46 and when the custom tibial cutting guide 20 is placed against the anterior surface portion 306 of the distal portion 304 of the tibia 300 with a portion of the reamer body 162 received within the tibial-talar space 342. Thus, when the cannulated reaming bit 190 is received within central channel 178, the shape of the custom tibial cutting guide 20 and the depth of the locator notch 46 in its distal end combine to set the alignment of the axial passage 192 of the cannulated reaming bit 190 with the central axis 302 of the tibia 300 for reaming of the tibia 300 along its central axis 302 with the reaming exterior front and side cutting threads 194, 196 of the cannulated reaming bit 190 as will be further delineated below. The diameter of the central channel 178 of the reamer body 162 is sized to closely receive and temporarily hold the cannulated reamer bit 190 which, in turn, is of the size needed to ream the tibial blind bore 328 for the size of the tibial. stem or, in one embodiment, the modular tibial stem components 372 of the size of the preoperatively chosen prosthesis 370.

Figure 26:
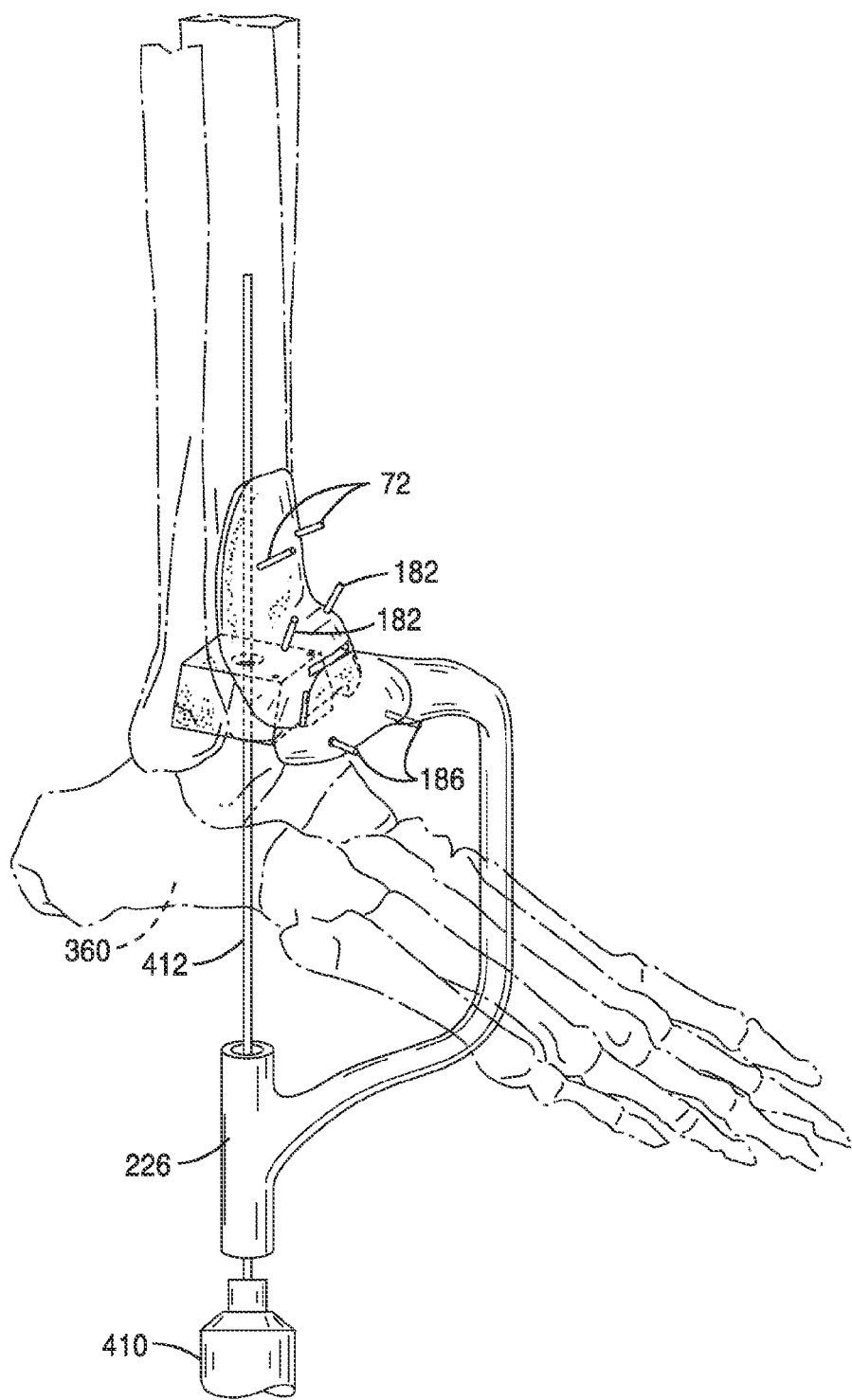
FIG. 26 is a front and side perspective view of the custom tibial cutting guide, the tibial reaming guide circumscribing the cannulated reaming bit, the C-shaped outrigger alignment guide, the K-wire, and the conventional surgical drill all relatively coupled together and to the prepared bone structure, and further illustrating the k-wire after being drilled up through the bottom of the calcaneus and the talus, through a central hole in the cannulated reaming bit, and then into the distal tibia for a predetermined distance along the central axis of the distal tibia.

Moreover, holes 180 in the body 162 of the tibial reaming guide 160 align with the reamer body fixation holes 62 (FIG. 2) disposed in the custom tibial cutting guide 20. Thin wires 182 are placed through the aligned holes to temporarily fix the custom tibial cutting guide 20 to the reamer body 162 (FIG. 26). Additionally, holes 184 disposed through the anterior face 174 of the reamer body 162 align with the fixation holes 211 disposed in the C-shaped outrigger alignment guide 200 for receiving thin wires 186 through the aligned holes to temporarily fix the C-shaped outrigger alignment guide 200 to the reamer body 162 anteriorly as illustrated in FIG. 26. Fixing the custom tibial cutting guide 20 to the anterior surface 306 of the distal portion 304 of the tibia 300 and to the reamer body 162 of the reaming guide 160, and then coupling the C-shaped outrigger alignment guide 200 to the custom tibial cutting guide 20 via the locator notch 64 and key 216 coupling and to the reamer body 162 via thin wires 186 provides stability for accurate reaming of the tibia 300 along its central axis as will be further delineated below.

In one embodiment, the tibial reaming guide 160 and the cannulated reaming bit 190 are made out of, but not limited to a metal material.

Outrigger Alignment Guide 200

Figure 13:
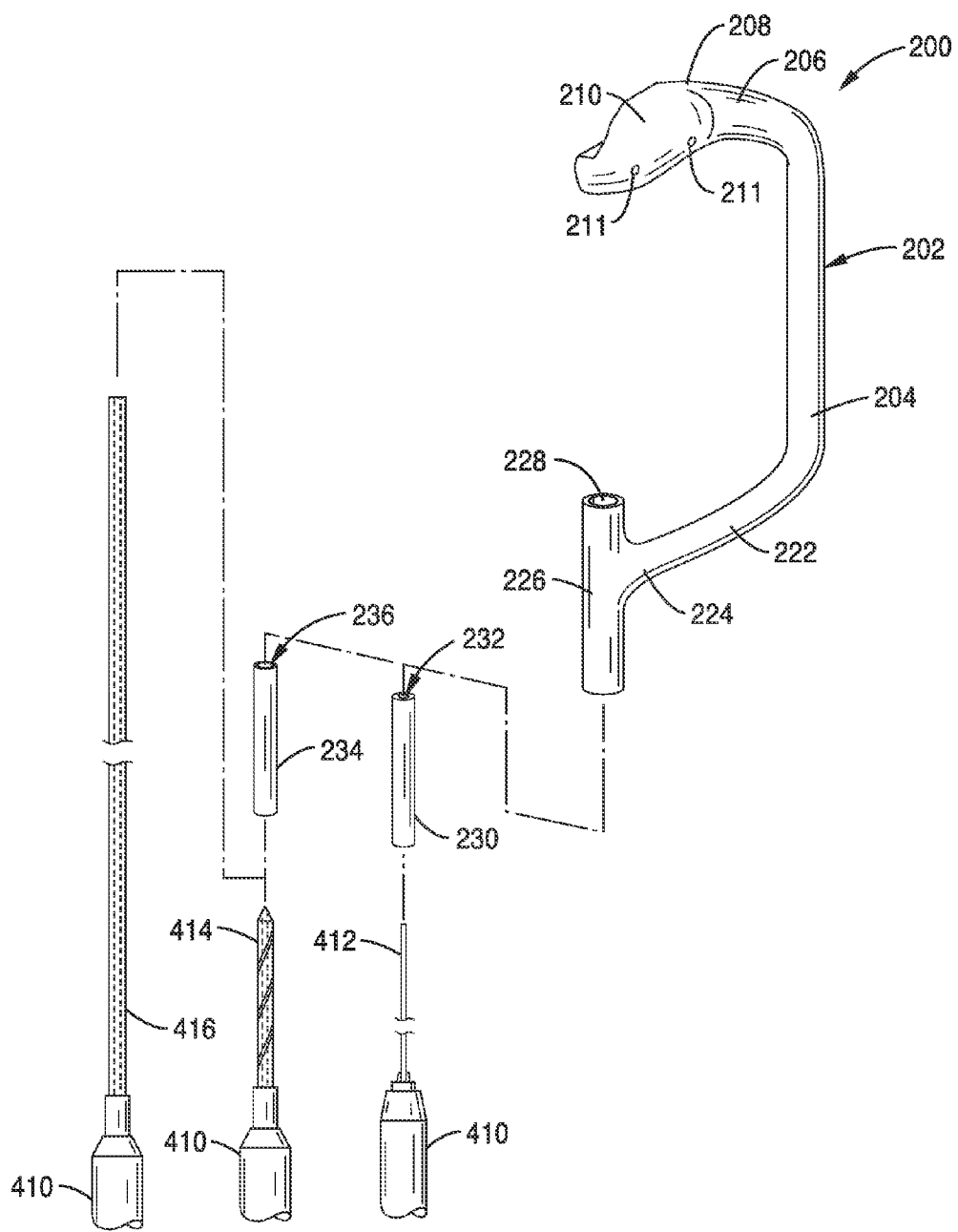
FIG. 13 is a front and side perspective view of the C-shaped outrigger alignment guide, the cylindrically shaped inner sleeve wire guide, the cylindrically shaped inner sleeve drill and driver bit guide, and further illustrating a thin wire or K-wire, a cannulated drill bit, and a cannulated reamer driver bit each coupled to a surgical drill.

Referring to FIG. 13, and in one embodiment, the system 10 is further comprised of the outrigger alignment guide 200. The outrigger alignment guide 200 is comprised of an arcuate or generally C-shaped body 202 comprised of a medial section 204 transitioning at one end to a superior section 206 and at the other end to an inferior section 222.

Figure 14:
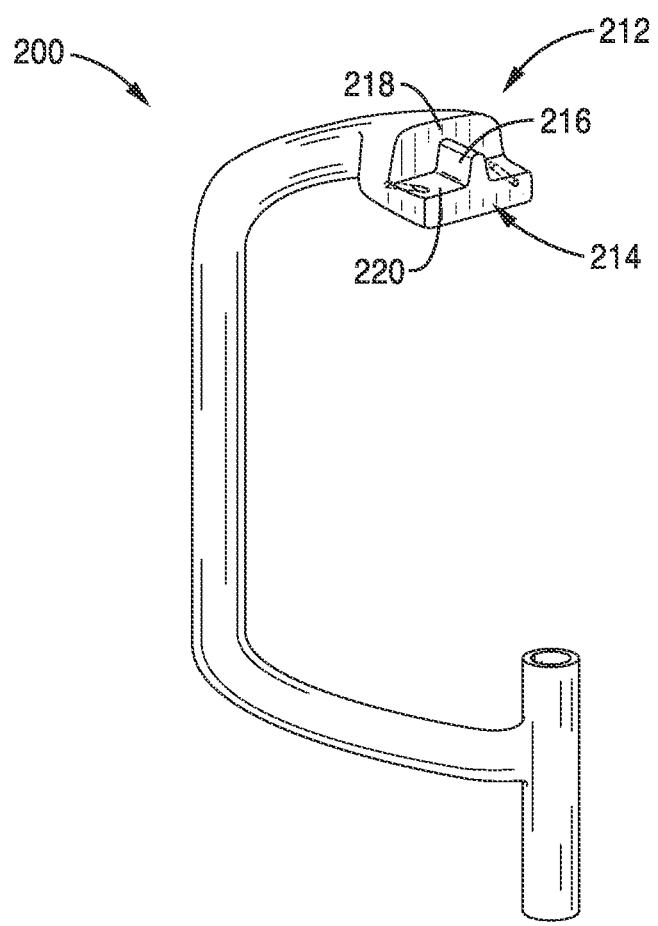
FIG. 14 is a back perspective view of the C-shaped outrigger alignment guide.

Referring to FIGS. 13 and 14, and in one embodiment, the superior section 206 generally perpendicularly extends away from the medial section 204 in substantially the same plane as the medial section 204, and then arches or bends out of the plane of the medial section 204 and transitions to a superior end 208 supporting an L-shaped bracket 210. In one embodiment, the L-shaped bracket 210 is integrally formed with the superior end 208 and is comprised of a superiorly extending sidewall 212 and a posteriorly extending base wail 214 that generally perpendicular extends from a distal end of the sidewall 212. The U-shaped bracket 210 is further comprised of a rectangular parallelepiped shaped ridge or key 216 that posteriorly extends from a posterior surface 218 of the sidewall 212 and superiorly extends from a superior surface 220 of the base wall 214. The rectangular parallelepiped shaped ridge or key 216 is sized to be received in the outrigger alignment guide locator notch 64 of the custom tibial cutting guide 20 for aligning the outrigger alignment guide 200 relative to the central long axis 302 of the tibia 300 when the custom tibial cutting guide 20 is coupled thereto. Additionally, the posterior surface 218 of the sidewall 212 is shaped to generally abut against a portion of the anterior surface 34 of the custom tibial cutting guide 20 that is generally below the superior tibial cutting slit 54 and generally between the lateral and medial cutting slits 56, 58 while the superior surface 220 of the base wall 214 is shaped to generally abut against the generally flat distal edge 26 of the generally half-bell-shaped body 22 of the custom tibial cutting guide 20.

The inferior section 222 generally perpendicularly extends away from the medial section 204 in substantially the same plane as the medial section 204, and then arches or bends out of the plane of the medial section 204 and transitions to an inferior end 224 supporting an inferior cylindrically shaped sleeve attachment 226 having an open ended cylindrically shaped bore 228 axially extending therethrough.

As illustrated in FIG. 13, the cylindrically shaped sleeve attachment 226 is integrally formed with and extends from both sides of the inferior end 224, and is spaced from and generally parallel with the medial section 204.

The open ended cylindrically shaped bore 228 of the sleeve attachment 226 is sized to closely receive two removable, alternate inner sleeve guides: the cylindrically shaped inner sleeve wire guide 230 having a open ended cylindrically shaped interior bore 232 extending therethrough and the cylindrically shaped inner sleeve drill and driver bit guide 234 having a open ended cylindrically shaped interior bore 236 extending therethrough.

The open ended cylindrically shaped interior bore 232 of the wire guide 230 is sized to closely receive and pass a thin wire such as a K-wire 412 therethrough and the open ended cylindrically shaped interior bore 236 of the drill and driver bit guide 234 is sized to closely receive and pass either a cannulated drill bit 414 or a cannulated driver hit 416 therethrough. The open ended cylindrically shaped interior bore 236 of the drill and driver bit guide 234 is of a larger diameter than the diameter of the open ended cylindrically shaped interior bore 232 of the wire guide 230.

In one embodiment, the outrigger alignment guide 200 is made out of but not limited to a metal material and is constructed as, but not limited to, an integrally formed one piece instrument. Additionally, and in one embodiment, the wire guide 230 and the drill and driver bit guide 234 are made out of, but not limited to a metal material.

Skeleton Cage 240 and Double Fork Cage 260

In one embodiment, the system 10 is further comprised of two metal instruments that are used as internal frames for providing temporary stability and alignment between the tibia 300 and talus 330 during the construction of the tibial stern 372 of the chosen prosthesis 370. Both instruments can be easily removed and re-inserted as needed to allow for easier passage of the components into the tibial-talar space 342.

Figure 15:
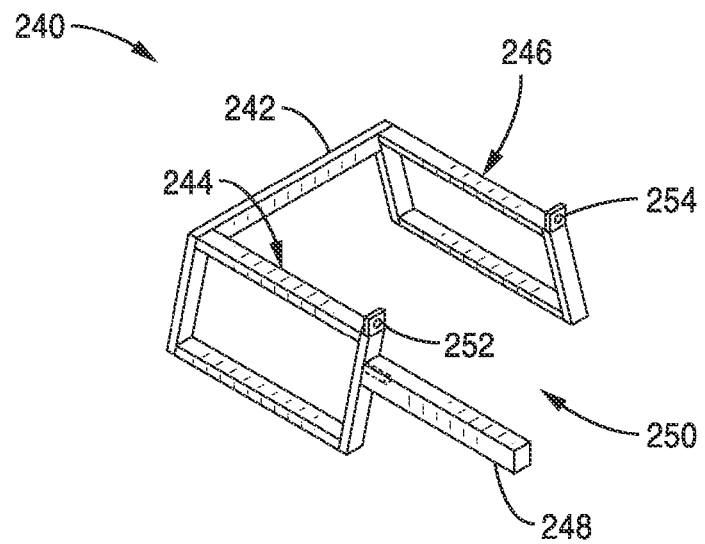
FIG. 15 is a perspective view of a skeleton cage or first frame that fits into a space between the prepared tibia and talus defining as a tibial-talar space for holding the bones apart with some stability while tibial stem components of a chosen prosthesis fit in place, and further illustrating a handle that aids in its insertion and removal and holes on its superior edges for use in temporary fixation to the tibia with wires or screws.

Referring to FIG. 15, a first internal frame is a skeleton cage 240 comprised of a posterior transverse member 242 rigidly connected between two superior portions of two spaced apart, rectangularly shaped, and inwardly slanting frames 244, 246 for providing the skeleton cage 240 with an external shape that is generally congruent with the generally pyramidal frustum shape of the tibial reaming guide 160 so as to fit snugly in the space between the tibia 300 and talus 330 defined as the tibial-talar space 342, In one embodiment, the skeleton cage 240 has an external handle 248 operatively connected to and extending from an anterior edge of at least one of frame members 244, 246 to aid in manipulating the skeleton cage 240 into and out of position. FIG. 15 illustrates the operative coupling of the external handle 248 to the outer frame member 244.

Figure 16:
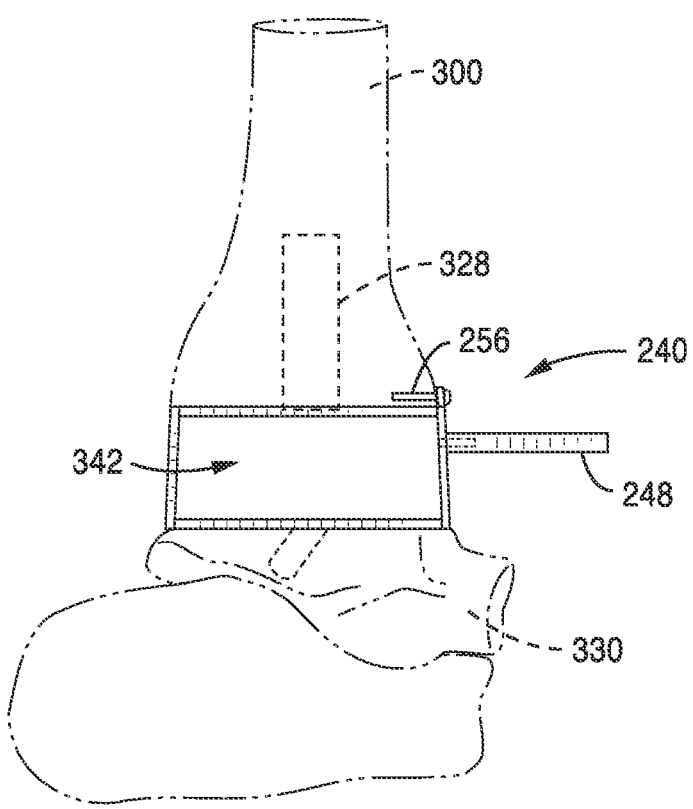
FIG. 16 is a side elevational view of the skeleton cage positioned into the tibial-talar space and removably attached to the tibia.

Referring to FIGS. 15 and 16, a central anterior open portion 250 of the skeleton cage or first frame 240 allows stern pieces of the modular tibial stem component 273 to be easily passed through skeleton cage 240 and into the tibial-talar space 342 for insertion into the blind bore 328 reamed in tibia 300. Additionally, the skeleton cage 240 is comprised of two perforated tabs 252, 254 that can be used to connect the skeleton cage 240 to the tibia via wires or screws 256.

Figure 17:
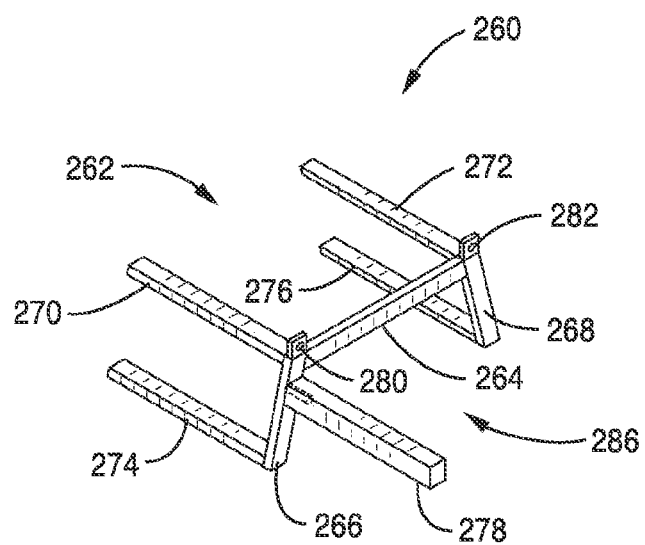
FIG. 17 is a perspective view of a double fork cage or second frame that fits into the tibial-talar space for holding the tibia and talus bones apart during the placement of a tibial tray, and further illustrating a handle that aids in its insertion and removal and holes on its superior edges for use in temporary fixation to the tibia with wires or screws.
Figure 18:
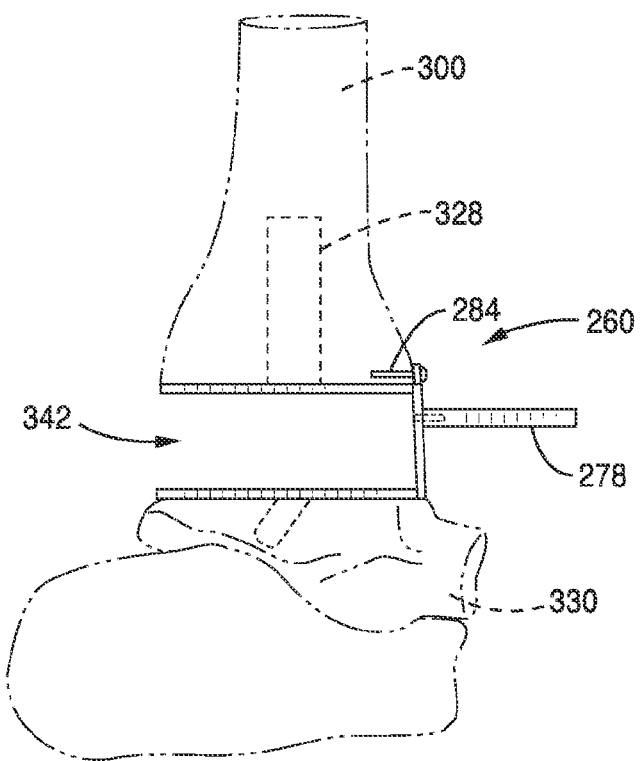
FIG. 18 is a side elevational view of the double fork cage positioned into the tibial-talar space and removably attached to the tibia.

Referring to FIGS. 17 and 18, a second internal frame is a double fork cage 260 comprised of an anterior frame 262 having three members outlining three sides of a trapezoid. Specifically, the anterior frame 262 is comprised of a superior base member 264 rigidly connected between superior ends of two spaced apart, non-parallel frame members 266, 268. The anterior frame 262 is substantially the size of the tibial-talar space 342. Additionally, the double fork frame 260 is comprised of four spaced apart, generally parallel tines 270, 272, 274, and 276 that are operatively coupled to and extend posteriorly off the anterior frame 262 into the superior medial, the superior lateral, the inferior medial and the inferior lateral edges of the tibial-talar space 342. The anterior frame 262 is further comprised of an external handle 278 that extends off an anterior face of one of three members 262, 264, or 266 to aid in manipulating the double fork frame 260 into and out of position. FIG. 17 illustrates the operative coupling of the external handle 278 to the frame member 266. Additionally, and in one embodiment, the double fork frame 260 is comprised of two perforated tabs 280, 282 that can be used to connect the frame 260 to the tibia via wires or screws 284.

In one embodiment, the double fork cage 260 is placed in the tibial-talar space 342 prior to coupling of the inferior tibial tray component 382 to the inferior stem piece 380 of the chosen prosthesis 370. Next, the inferior tibial tray component 382 is passed through a central anterior open portion 286 of the double fork cage 260 and coupled to the inferior stem piece 380. Then, the double fork cage 260 is removed prior to the tray 382 being seated into its final position.

Use and Operation

Preoperative Process

In use and operation, and referring to the drawings, the morphology of an ankle being replaced is preoperatively assessed radiographically using the computer imaging system 22 for obtaining radiographic information or data 124. This radiographic information or data is transformed into a virtual 3-dimensional copy or model 140 of the ankle with the existing 3-D modeling software 138 of the computer modeling system 130. The 3-D modeling software 138 then analyzes the virtual ankle model 140 and chooses one prostheses size 360 from a plurality of available sizes of existing prosthesis 362 and determines where the bones should be cut and reamed as a function of transformed radiographical preoperative analysis of the ankle and the chosen size of the prosthesis. Accordingly, the process of choosing one of a plurality of available sizes of existing prosthesis and determining the associated bone cuts correlative to the chosen size of the prosthesis is done preoperatively by utilizing the radiographic information or data 124 obtained by the computer imaging system 122 and the analysis provided by the computer modeling system 130.

Next, the computer or numerically controlled machine system 150 molds the custom tibial cutting guide 20 out of, for example, plastic and mills the guide 20 to fit precisely against the anterior surface portion 306 of the distal portion 304 of the tibia 300 as a function of the computer analysis. Additionally, and also as a function of the computer analysis, the computer or numerically controlled machine system 150 molds the custom talar cutting guide 80 out of for example, plastic and mills the guide 80 to fit precisely on the talar dome 332 and against the dorsum of the talar neck 336. Furthermore, and as delineated in detail hereinabove, the custom cutting guides 20, 80 are milled with precisely oriented slits that guide the position of saw blades, and holes for drill bits, reamer bits, and fixation pins or screws so that when each guide 20, 80 is coupled to its respective bone in its unique position, the slits and holes are in the preoperatively defined position for each of them.

Tibia Cuts

In one embodiment, and referring to FIGS. 2 through 4, 19 and 20, the custom tibial cutting guide 20 is utilized first and, like a lock, the first posterior surface portion 42 of the custom tibial cutting guide 20 matches the anterior surface portion 306 of the distal portion 304 of the tibia 300 in one unique position. In this unique position, the cutting slits 54, 56, and 58 along with the bone fixation holes 60, the reaming guide locator notch 46, and the alignment guide locator notch 64 are in their preoperatively defined positions. In one embodiment, the custom tibial cutting guide 20 covers the distal 4-6 cm of the tibia 300 and spans the anterior ankle from the medial malleolus to the interior side of the lateral malleolus. Once the custom tibial cutting guide 20 is fitted to the distal portion 304 of the tibia 300, screws or wires 72 are passed through the plurality of fixation holes 62 in the guide 20 so that it can be temporarily fixed to the tibia bone 300. Then, the tibia saw blade 402 (FIG. 20) is placed through the precisely placed slits 54, 56, and 58 of the guide 20 and powered by the saw 400 for making the preoperatively defined cuts in the tibia 300. After the tibia bone cuts have been made, the screws or wires 72 are taken out, and the custom tibial cutting guide 20 is removed and saved for later use with the tibial reaming guide 160. The pieces of cut tibia bone are then removed.

Talus Cuts

Referring to FIGS. 5 through 7, and 21 through 23, the custom talar cutting guide 80 is utilized next and, like a lock, the inferior surface 96 of the cutting guide 80 matches, in one unique position, the surface 334 of the talar dome 332 and the posterior surface 108 of the cutting guide 80 matches, in one unique position, about three to four centimeters of the dorsum 338 of the talar neck 336. In this unique position, the angled reaming channel 100, the cutting slit 112 and the bone fixation holes 114, 116 are in their preoperatively defined positions. Once the custom talar cutting guide 80 is fitted to the talus 330, screws or wires 350 are passed through the plurality of fixation holes 116 in the guide 80 so that it can be temporarily fixed to the talus bone 330. Then, the talus saw blade 406 is placed through the precisely placed slit 112 of the guide 80 and powered by the saw 400 for making the preoperatively defined cut of the top of the talus bone 330.

After the top of the talus 330 is cut, screws or wires 346 can be passed through the plurality of fixation holes 114 in the guide 80 so that the cut top of the talus 330 is held in place.

Next, the drill or reamer bit 422 is placed through the angled reaming channel 100 and powered by drill 420 for reaming the talus 330 to a preoperatively determined depth achieved by utilizing, for example, a stop collar 424 disposed on the reaming bit 422 or a precisely sized reaming bit 422.

Then, the wires or screws 346, 350 are taken out, and the custom talar cutting guide 80 is removed, and the cut piece of talus bone taken away thereby forming the trapezoidally shaped tibial-talar space 342 (EEG. 24) between the tibia 300 and the talus 330.

Angular Deformity Correction

It is important to note that the two separate custom guides 20, 80 provide the means for correcting any angular deformity of the ankle and for preparing the bones of the ankle to receive a chosen prosthesis 370 in the proper orientation that precludes the prosthesis 370 from being angled one way or another and, as a result, precludes the patient from walking on one side or the other of the foot thereby abating stress in different areas of the prosthesis 370 that results in the components of the prostheses 370 failing or wearing out prematurely. The goal is for the prosthesis to last for decades. Accordingly, the two separate custom cutting guides 20, 80 can correct for any angular deformity of the ankle by making cuts in the tibia 300 and a cut in the talus 330 that are related to each respective bone itself and not one another. So when the cuts are made with the custom cutting guides 20, 80, the surfaces are substantially flat. Specifically, the custom cutting guides 20, 80 respectively dictate that the superior cut 310 on the tibia 300 is substantially perpendicular to the long central axis 302 of the tibia 300 and that the cut 340 of the talus is parallel to the bottom of the foot as it rest on the ground and also perpendicular to the long central axis 302 of the tibia 300.

Tibial Reaming Guide 160 & Outrigger Alignment Guide 200

Referring to FIGS. 3, 10, 25, and 26, the tibial reaming guide 160 is used next to prepare the tibia 300 for an intramedullary stern component which, in one embodiment, is the modular tibial stem component 372 of the prosthesis 370. The modular tibial stem component 372 is designed to fit in the center of the tibia 300, and is oriented along its long central axis 302.

As noted above, the size of the tibial reaming guide 160 is preoperatively selected to correspond to the size of the preoperatively chosen prosthesis 370 and has a predetermined size for fitting against the reaming guide locator notch 46 of the custom tibial cutting guide 20, which determines its proper placement t for reaming the tibia 300 along its central axis 302, Additionally, the reamer body 162 of the tibial reaming guide 160 is designed to fit into the trapezoidally shaped tibial-talar space 342 after the resected tibial and talar bone segments have been removed.

The cannulated reamer bit 190 having a size that is needed to ream the distal tibia for the size of the chosen tibial stern 372 is removably fitted within the central channel 178 of the reamer body 162 of the tibial reaming guide 160. The reamer body 162 of the tibial reaming guide 160 is placed into the reaming guide locator notch 46 of the custom tibial cutting guide 20 such that the anterior face 174 of the body 162 fits against the second posterior surface portion 44 of the custom tibial cutting guide 20. The holes 180 in the body 162 align with holes 62 in the lower part of the custom tibial cutting guide 20. Thin wires 182 can then be placed through these holes to temporarily fix the custom tibial cutting guide 20 to the reamer body 162 (FIG. 26) of the tibial reaming guide 160.

Next, the tibial reaming guide 160 holding the cannulated reaming bit 190 is positioned into the trapezoidally shaped tibial-talar space 342 and the custom tibial cutting guide 20 is fixed to the distal tibia by wires or screws 72 passing through the bone fixation holes 60 of the guide 20 and into the holes 318 (FIG. 4) in the distal tibia. Positioning the tibial reaming guide 160 into the tibial-talar space 342 and fixing the custom tibial cutting guide 20 to the anterior distal tibia aligns the cannulated reaming bit 190 in the central channel 178 of tibial reaming guide 160 with the central axis 302 of the tibia 300. Thus, the shape of the custom tibial cutting guide 20 and the depth of the locator notch 46 in its distal end, combine to set the alignment of a central axis of central channel 178 coincident with the central axis 302 of the tibia 300.

Now, the bracket 210 of the outrigger alignment guide 200 is coupled to the custom tibial cutting guide 20 by frictionally fitting the generally rectangular parallelepiped shaped ridge or key 216 of the bracket 210 into the outrigger alignment guide locator notch or keyway notch 64 disposed in the distal end of the custom tibial cutting guide 20 and abutting the posterior surface 218 of the bracket 210 against the anterior surface 34 of the custom tibial cutting guide 20. Wire or screws 182 are then passed through bracket holes 211 into the reamer body 162 of the tibial reaming guide 160 via reamer body holes 184.

Once the C-shaped outrigger alignment guide 200 is in place, and by design, the inferior sleeve attachment 226 of the outrigger alignment guide 200 is located just off of the skin of the sole of the foot and the center of the inferior sleeve attachment 226 is aligned with the center of the channel 178 of the tibial reaming guide 160 as illustrated in FIG, 26.

Next, the inner sleeve wire guide 230 is placed through the bore 228 of the inferior sleeve attachment 226 (FIG, 13) and a thin wire 412 such as a k-wire is powered by drill 410 and drilled up through the inner sleeve wire guide 230, through a cut in the skin, then from the base of the calcaneus 360 through the talus 330 and through central opening 192 in the cannulated reamer bit 190 held in the central channel 178 of the tibial reaming guide 160. The wire 412 continues to pass proximally into the tibia 300. The passage of the thin wire 412 through the inner sleeve wire guide 230 supported in the inferior sleeve attachment 226 of the outrigger alignment guide 200 and then through the cannulated reamer bit 190 will guide the thin wire 412 proximally along the central axis 302 of the tibia 300.

Figure 27:
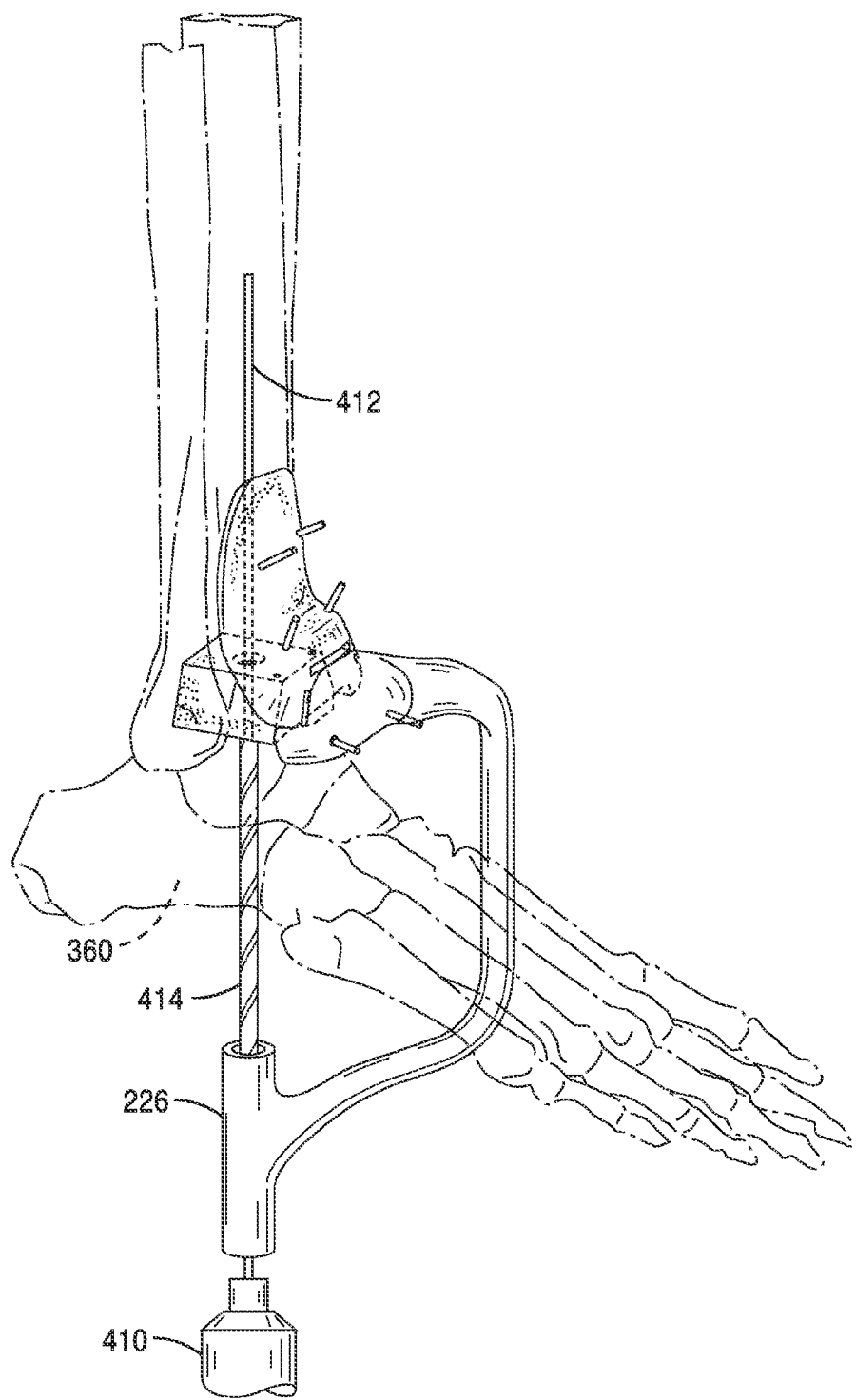
FIG. 27 is a front and side perspective view of the custom tibial cutting guide, the tibial reaming guide circumscribing the cannulated reaming bit, the C-shaped outrigger alignment guide, the cannulated drill bit, and the conventional surgical drill all relatively coupled together and to the prepared bone structure, and further illustrating the cannulated drill bit after being drilled over the K-wire passing through the cannulated drill bit, up through the bottom of the calcaneus and the talus, and up to the central hole in the cannulated reaming bit along the central axis of the distal tibia.

Referring to FIG. 27, and with the thin wire 412 left in place, the inner sleeve wire guide 230 is removed, and the inner sleeve drill and driver bit guide 234 having the larger cylindrically shaped bore 236 is placed through the bore 228 of the inferior sleeve attachment 226 (MG. 13) for guiding and allowing passage of the cannulated drill bit 414 through the inner sleeve drill and driver bit guide 234 for being powered by the drill 410 for drilling over the thin wire 412 through the inferior sleeve attachment 226, the calcaneus 360, and the talus 330 and then, up to the base of the cannulated reamer bit 190 in the central channel 178 of the tibia reaming guide 160.

Then, the cannulated drill bit 414 is removed, again leaving the thin wire 412 in place. The drilling of the calcaneus 360 and talus 330 leaves a wider passage through those bones.

Figure 28:
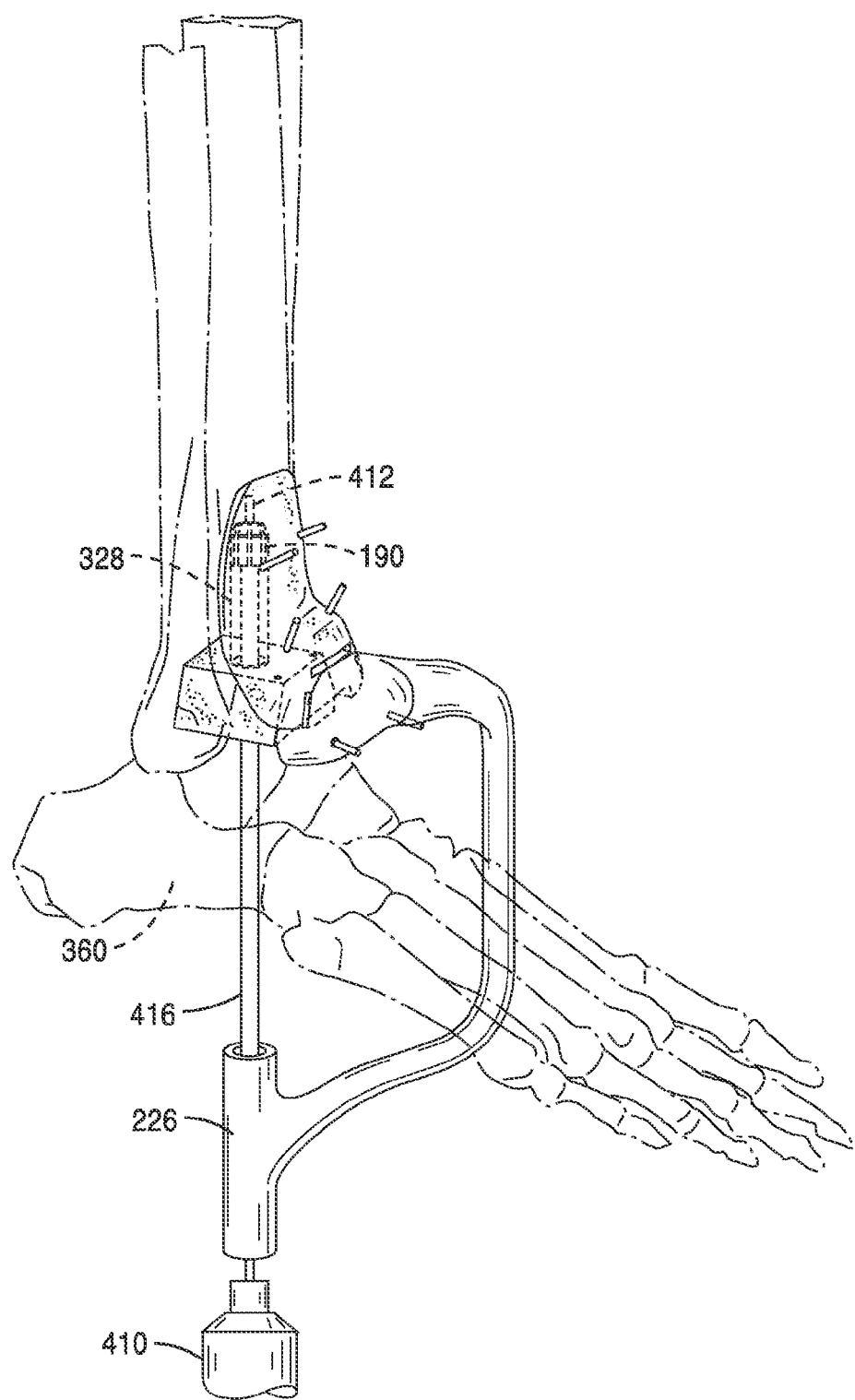
FIG. 28 is a front and side perspective view of the custom tibial cutting guide, the tibial reaming guide circumscribing the cannulated reaming bit, the C-shaped outrigger alignment guide, the cannulated reamer driver bit, and the conventional surgical drill all relatively coupled together and to the prepared bone structure, and further illustrating the cannulated reamer driver bit after being drilled over the K-wire passing through the cannulated drill bit, up through the bottom of the calcaneus and the talus, and after capturing and driving the cannulated reaming bit along the central axis of the distal tibia for forming a blind bore in the tibia for a tibial stem of a ankle prosthesis.

Finally, and referring to FIG. 28, the cannulated reamer shaft or drive 416 with diameter less than the drill bit is passed over the thin wire 412 and up through the inner sleeve drill and driver bit guide 234 in the inferior sleeve attachment 226, the calcaneus 360, and the talus 330 to capture the cannulated reamer bit 190 in the central channel 178 of the tibial reamer guide 160. The distal tibia 304 can then be reamed over the thin wire 412 and along the central axis 302 of the tibia 300 forming the tibia blind bore 328 sized to receive the tibial intramedullary stem 372 of the chosen prosthesis 370.

At the completion of the tibial reaming, the cannulated reamer shaft or drive 416 and thin wire 412 are removed, the temporary fixation wires or screws 72, 182, and 186 are removed, and the custom tibial cutting guide 20, the reaming guide 160, and the C-shaped outrigger alignment guide 200 are removed.

Figure 29:
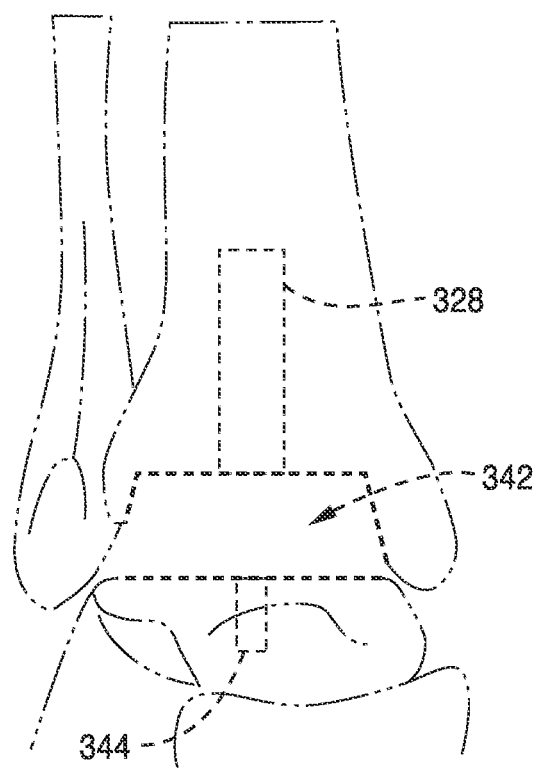
FIG. 29 is a front elevational view illustrating the bone cuts, the tibial blind bore, and the talar blind bore for a chosen size of ankle prosthesis.

At this point, and referring to FIG. 29, the tibia and talus cuts have been made for forming the tibial-talar space 342 and the tibia and talus have been reamed for forming the respective blind bores 328 and 344, Hence, the bones are prepared for placement of the preoperatively chosen total ankle prosthesis such as, but not limited to, the INBONE Total Ankle prosthesis 370 illustrated in FIG. 30. The INBONE Total Ankle prosthesis 370 is sold by Wright Medical Technology, Inc. (5677 Airline Road, Arlington, Tenn. 38002, USA) under the trademark INBONE Total Ankle System and is presently available in five sizes (number 2, 3, 4, 5, or 6), left and right.

In one embodiment, and referring to FIG. 30, the prosthesis 370 is comprised of modular tibial stem component 372, tibial tray component 382, poly insert component 384, talar dome component 388, and talar stem component 390. In one embodiment, the modular tibial stem component 372 is comprised of superior stem piece 374, first medial stem piece 376, second medial stem piece 378, and inferior stem piece 380. The stem pieces range from. 14-18 mm in diameter with a typical 4-piece construct measuring 50 mm in length. This is completely customizable per individual patient need. The segmented design allows for a less invasive approach and more robust anchoring. The talar stem component 390 extends at a precise angle inferiorly away from the talar dome component 388 and has 10 mm diameter and is available in 10 and 14 mm lengths.

The general technique or algorithm that is used during surgery for the placement of the prosthesis 370 is as follows.

Figure 31:
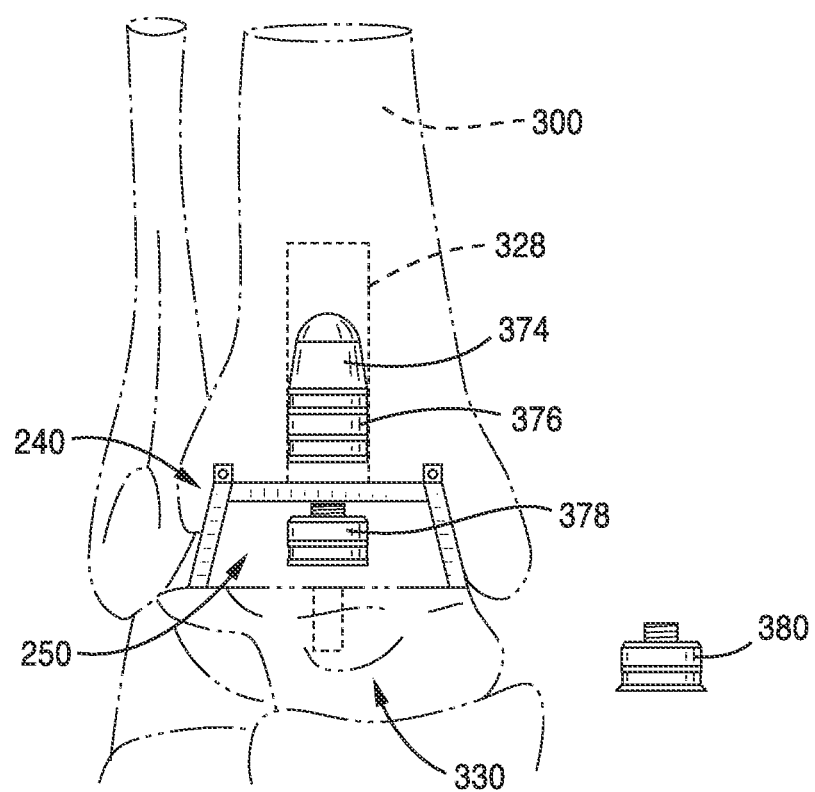
FIG. 31 is a front elevational view of the skeleton cage positioned into the tibial-talar space and removably attached to the tibia, and further illustrating its use during the placement of tibial stem components of the ankle prosthesis illustrated in FIG. 30.

Initially, and referring to FIGS. 30 and 31, the skeleton cage or first frame 240 having an external shape congruent with the tibial reaming guide 160 is fit snugly in the tibial-talar space 342 (FIG. 29) to keep the tibia 300 and talus 330 separated and stabilized. In one embodiment, the skeleton cage 240 employs external handle 248 (FIG. 16) to aid in manipulating it into and out of position and employs two perforated tabs 252, 254 to connect the skeleton cage 240 to the tibia via wires or screws 256. The central anterior open portion 250 of the skeleton cage 240 allows the superior stem piece 374, the first medial stem piece 376, the second medial stem piece 378, and the inferior stem piece 380, to be easily and successively passed therethrough and into the tibial blind bore 328 in the distal portion of the tibia 300 with each stem piece being screwed into the stem piece preceding it. Upon completion, the skeleton cage 240 is removed from the tibial-talar space 342.

Figure 32:
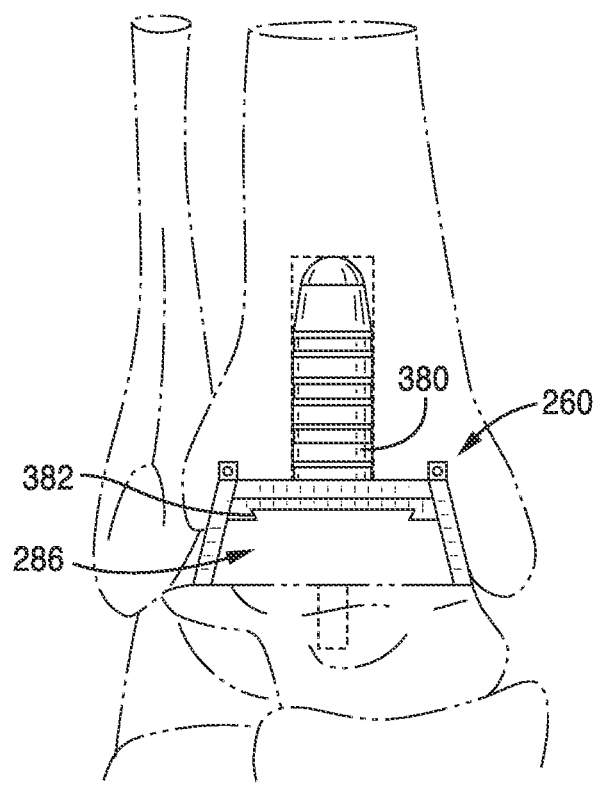
FIG. 32 a front elevational view of the double fork cage positioned into the tibial-talar space and removably attached to the tibia, and further illustrating its use during the placement of a tibial tray of the ankle prosthesis illustrated in FIG. 30.

Next, and referring to FIGS. 30 and 32, the double fork cage or second frame 250 having an external shape congruent with the tibial reaming guide 160 is fit snugly in the tibial-talar space 342 (FIG. 29) to keep the tibia and talus separated and stabilized. In one embodiment, the double fork cage 250 employs external handle 278 (FIG. 18) to aid in manipulating it into and out of position and employs two perforated tabs 280, 282 to connect the double fork cage 250 to the tibia via wires or screws 284. The central anterior open portion 286 of the double fork cage 250 allows the tibial tray component 382 to be easily passed therethrough and partially coupled to the inferior stem piece 380. Then, the double fork cage 250 is removed from the tibial-talar space 342 and the coupling of the tibial tray component 382 to the inferior stem piece 380 is completed.

Figure 33:
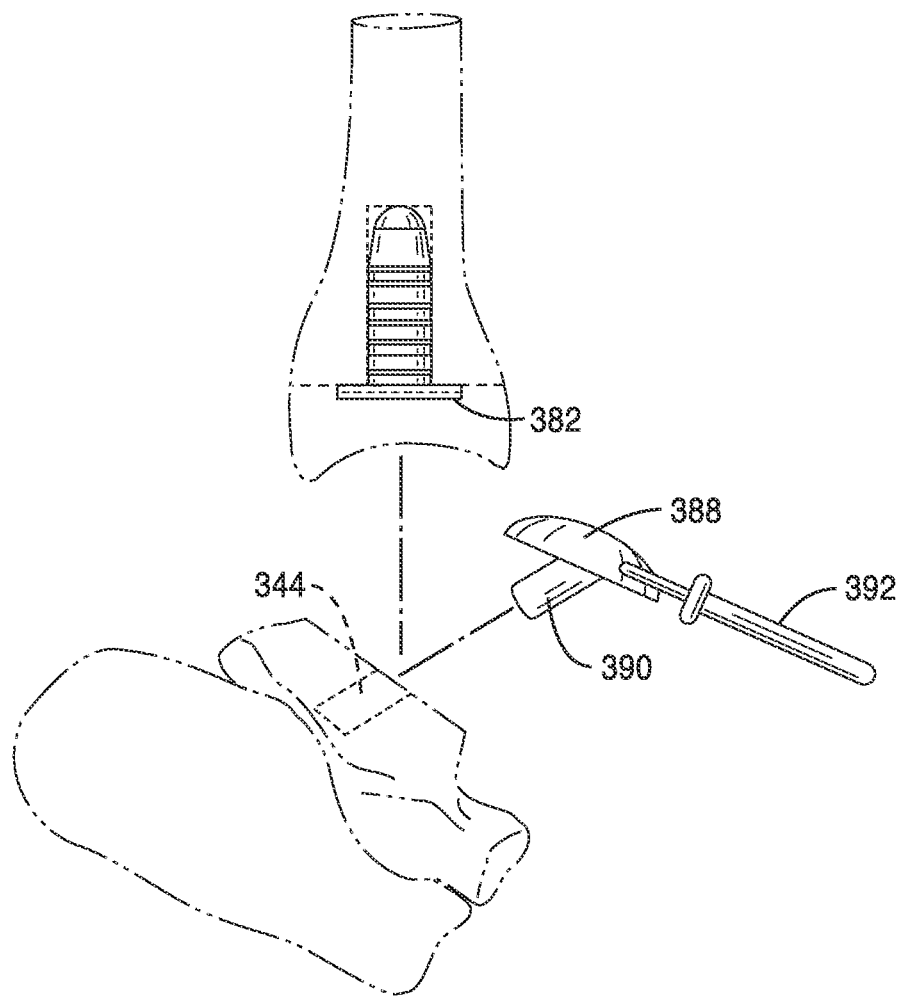
FIG. 33 is a side elevational view illustrating a method step of fitting the talus with the talar dome and stem of the ankle prosthesis illustrated in FIG. 30.

Now referring to FIGS. 30 and 33, the talar stem component 390 is coupled into the pre-drilled talar blind bore 344 followed by using a talar dome holding tool 392 along with a strike tool system to couple the talar dome component 388 to the talar stem component 390.

Figure 34:
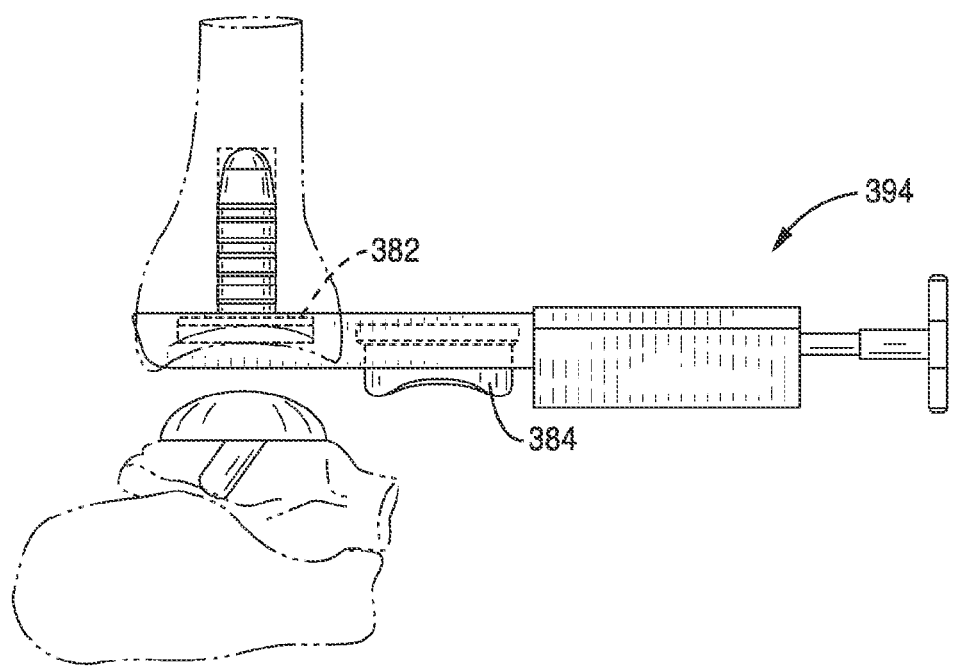
FIG. 34 is a side elevational view illustrating a method step of fitting a poly insert for completion of the replacement of a total ankle with the ankle prosthesis illustrated in FIG. 30.
Figure 35:
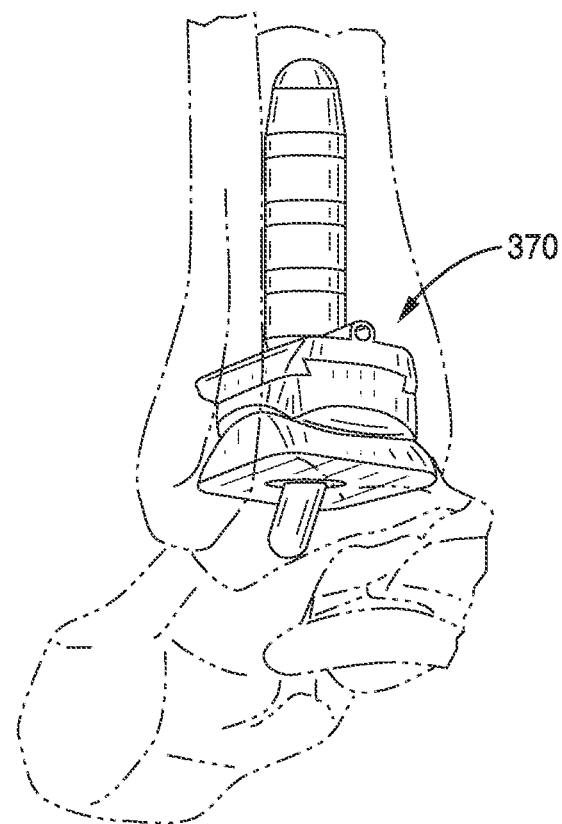
FIG. 35 is a side and front perspective view of the replacement of the total joint with the ankle prosthesis illustrated in FIG. 30.

Finally, and referring to FIGS. 30 and 34, the poly insert component 384 is coupled to the tibial tray component 382 utilizing a poly insertion tool system 394 thereby completing the total ankle replacement with the prosthesis 370 as illustrated in FIG. 35.

Accordingly, and in one aspect, the system 10 improves the precision of bone cuts, eliminates the need for a large external frame to hold the ankle immobile, simplifies the operative procedure, decreases the operative time, minimizes the need for intra-operative fluoroscopy and allows better correction of deformities by independent bone cuts and reaming of the tibia and talus bones.

The above delineation of the system 10, including its use and operation, demonstrate the industrial applicability of this invention.

Moreover, having thus described the present invention, it should be apparent that numerous modifications and adaptations may be resorted to without departing from the scope and fair meaning of the present invention as set forth hereinabove and as described hereinbelow by the claims.

I claim:

1. A cutting guide system for use in total ankle replacement surgery, said system comprising:
    a tibial reaming guide comprising a tibial reaming guide body sized to fit in a space formed by a resected segment of a distal portion of a tibia and a resected segment of a dome of a talus, said tibial reaming guide body having a superior face, an inferior face, and an opened ended channel extending through said tibial reaming guide body between said superior and inferior faces;
    a cannulated removable reaming bit removably received within said opened ended channel of said tibial reaming guide body; and said cannulated removable reaming bit having a bone reaming exterior surface for forming a bore in the tibia when driven wherein said bore is sized to receive an intramedullary stem of a preoperatively chosen ankle prosthesis.

2. The system of claim 1 further comprising a tibial guide having a first posterior surface portion and a second posterior surface portion anteriorly recessed from said first posterior surface portion at a preoperatively defined distance from a central longitudinal axis of the tibia for defining a tibial reaming guide locator notch anteriorly recessed from said first posterior surface portion and configured to receive at least a portion of said tibial reaming guide to locate said cannulated removable reaming bit relative to the central longitudinal axis of the tibia by said tibial guide being abutted against the distal portion of the tibia.

3. The system of claim 2 further comprising an alignment guide comprising a generally arcuate body having a medial section transitioning to a superior end supporting a locating member and to an inferior end supporting a sleeve attachment wherein said locating member is coupled to said tibial guide for locating said sleeve attachment just off of a sole of a foot of the patient while aligning said sleeve attachment relative to the central longitudinal axis of the tibia by said tibial guide being abutted against the distal portion of the tibia.

4. The system of claim 3 wherein a wire is passed through said sleeve attachment to guide drilling of the wire up through a bottom of a calcaneus and the talus, through a central hole in said cannulated removable reaming bit circumscribed by said tibial reaming guide, and into the distal portion of the tibia for a predetermined distance along the central longitudinal axis of the tibia.

5. The system of claim 4 wherein a cannulated drill bit is passed through said sleeve attachment to guide driving of the cannulated drill bit over the wire and up through the bottom of the calcaneus and the talus and up to said central hole in said cannulated removable reaming bit for forming a drill bore extending from the bottom of the calcaneus to and in open communication with said central hole in said cannulated removable reaming bit.

6. The system of claim 5 wherein a cannulated reamer drive bit is passed through said sleeve attachment to guide passing the cannulated reamer drive bit into engagement with said central hole in said cannulated removable reaming bit and driving said cannulated removable reaming bit over the wire and along a predetermined distance of the central longitudinal axis of the tibia to ream a tibial blind bore into the distal portion of the tibia wherein the tibial blind bore is sized to receive a tibial stem of a preoperatively chosen size of an ankle prosthesis.

7. A cutting guide system for use in total ankle replacement surgery, said system comprising:
a tibial reaming guide sized to fit in a space formed by a resected segment of a distal portion of a tibia and a resected segment of a dome of a talus, said tibial reaming guide having a opened ended channel;
a cannulated removable reaming bit removably received within said opened ended channel of said tibial reaming guide;
said cannulated removable reaming bit having a bone reaming exterior surface for forming a bore in the tibia when driven wherein said bore is sized to receive an intramedullary stem of a preoperatively chosen ankle prosthesis; and
wherein said tibial reaming guide has a generally pyramidal frustum shaped reamer body comprised of a rectangularly shaped superior face and a rectangularly shaped inferior face.

8. The system of claim 7 wherein said opened ended channel of said tibial reaming guide has a central axis substantially perpendicular to said rectangularly shaped superior face and said rectangularly shaped inferior face.

9. The system of claim 8 further comprising means for locating said tibial reaming guide in the space formed by the resected segment of the distal portion of the tibia and the resected segment of the dome of the talus to centrally locate said cannulated reaming bit relative to a central longitudinal axis of the tibia.

10. A cutting guide system for use in total ankle replacement surgery, said system comprising:
a tibial reaming guide comprising a tibial reaming guide body sized to fit in a space formed by a resected segment of a distal portion of a tibia and a resected segment of a dome of a talus, said tibial reaming guide body having a superior face, an inferior face, and an opened ended channel extending through said tibial reaming guide body between said superior and inferior faces;
said tibial reaming guide body having a taper from wide to narrow from said inferior face to said superior face of said tibial reaming guide body;
a cannulated removable reaming bit removably received within said opened ended channel of said tibial reaming guide body; and
said cannulated removable reaming bit having a bone reaming exterior surface for forming a bore in the tibia when driven wherein said bore is sized to receive an intramedullary stem of a preoperatively chosen ankle prosthesis.

11. The system of claim 10 wherein said opened ended channel of said tibial reaming guide body has a central longitudinal axis substantially perpendicular to said superior face and said inferior face.

12. The system of claim 10 further comprising means for locating said tibial reaming guide in the space formed by the resected segment of the distal portion of the tibia and the resected segment of the dome of the talus to centrally locate said cannulated reaming bit relative to a central longitudinal axis of the tibia.

* * * * *